US008785211B2

(12) United States Patent
Bayley et al.

(10) Patent No.: US 8,785,211 B2
(45) Date of Patent: *Jul. 22, 2014

(54) METHODS USING PORES

(75) Inventors: Hagan Bayley, Oxford (GB); Yann Astier, Oxford (GB); Orit Braha, Oxford (GB)

(73) Assignee: Isis Innovation Limited, Oxford (GB)

( * ) Notice: Subject to any disclaimer, the term of this patent is extended or adjusted under 35 U.S.C. 154(b) by 13 days.

This patent is subject to a terminal disclaimer.

(21) Appl. No.: 13/338,794

(22) Filed: Dec. 28, 2011

(65) Prior Publication Data

US 2012/0219960 A1 Aug. 30, 2012

Related U.S. Application Data

(63) Continuation of application No. 12/093,610, filed as application No. PCT/GB2006/004265 on Nov. 15, 2006, now Pat. No. 8,105,846.

(30) Foreign Application Priority Data

Nov. 15, 2005 (GB) .................................. 0523282.2

(51) Int. Cl.
C12Q 1/68 (2006.01)
G01N 33/543 (2006.01)
G01N 27/26 (2006.01)

(52) U.S. Cl.
USPC ............................ 436/518; 435/6.1; 204/400

(58) Field of Classification Search
CPC ........... C12Q 1/6869; C12Q 2565/631; G01N 33/48721
See application file for complete search history.

(56) References Cited

U.S. PATENT DOCUMENTS

| | | | |
|---|---|---|---|
| 5,777,078 A | 7/1998 | Bayley et al. | |
| 5,795,782 A | 8/1998 | Church et al. | |
| 5,817,771 A | 10/1998 | Bayley et al. | |
| 6,015,714 A | 1/2000 | Baldarelli et al. | |
| 6,123,819 A | 9/2000 | Peeters | |
| 6,127,166 A | 10/2000 | Bayley et al. | |
| 6,251,610 B1 | 6/2001 | Gupte et al. | |
| 6,362,002 B1 | 3/2002 | Denison et al. | |
| 6,426,231 B1 | 7/2002 | Bayley et al. | |
| 6,451,563 B1 | 9/2002 | Wittig et al. | |
| 6,627,067 B1 | 9/2003 | Branton et al. | |
| 6,824,659 B2 | 11/2004 | Bayley et al. | |
| 6,863,833 B1 | 3/2005 | Bloom et al. | |
| 6,916,665 B2 * | 7/2005 | Bayley et al. | ................. 436/149 |
| 6,927,070 B1 | 8/2005 | Bayley et al. | |
| 7,087,729 B1 | 8/2006 | Prive | |
| 7,189,503 B2 | 3/2007 | Akeson et al. | |
| 8,105,846 B2 * | 1/2012 | Bayley et al. | ................. 436/518 |
| 2002/0028458 A1 | 3/2002 | Lexow | |
| 2002/0094526 A1 | 7/2002 | Bayley et al. | |
| 2003/0044816 A1 | 3/2003 | Denison et al. | |
| 2003/0099951 A1 | 5/2003 | Akeson et al. | |
| 2003/0108902 A1 | 6/2003 | Abarzua | |
| 2003/0211502 A1 | 11/2003 | Sauer et al. | |
| 2003/0215881 A1 | 11/2003 | Bayley et al. | |
| 2004/0214177 A1 | 10/2004 | Bension | |
| 2005/0053961 A1 | 3/2005 | Akeson et al. | |
| 2005/0260655 A1 | 11/2005 | Liu et al. | |
| 2007/0015182 A1 | 1/2007 | Abarzua | |
| 2008/0311582 A1 | 12/2008 | Bayley et al. | |
| 2009/0298075 A1 | 12/2009 | Travers et al. | |
| 2011/0177498 A1 * | 7/2011 | Clarke et al. | ................... 435/6.1 |
| 2011/0229877 A1 | 9/2011 | Jayasinghe et al. | |

FOREIGN PATENT DOCUMENTS

| | | |
|---|---|---|
| GB | 2130219 | 5/1984 |
| GB | 2453377 | 4/2009 |
| JP | 11-137260 | 5/1999 |
| WO | 99/05167 A1 | 2/1999 |
| WO | 00/28312 A1 | 5/2000 |
| WO | 01/40516 A2 | 6/2001 |
| WO | 01/42782 A1 | 6/2001 |
| WO | 01/59453 A2 | 8/2001 |
| WO | 02/42496 A2 | 5/2002 |
| WO | 03/095669 A1 | 11/2003 |
| WO | 2005/056750 A2 | 6/2005 |
| WO | 2006/020775 A2 | 2/2006 |
| WO | 2006/028508 A2 | 3/2006 |
| WO | 2006/100484 A2 | 9/2006 |
| WO | 2007/057668 A1 | 5/2007 |
| WO | 2007/075987 A2 | 7/2007 |
| WO | 2007/084103 A2 | 7/2007 |
| WO | 2008/045575 A2 | 4/2008 |

(Continued)

OTHER PUBLICATIONS

Cudic P. et al. J. Chem. Soc., Chem. Commun., 1995, p. 1073-1075.*
Akeson, Mark et al., "Microsecond Time-Scale Discrimination Among Polycytidylic Acid, Polyadenylic Acid, and Polyuridylic Acid as Homopolymers or as Segments Within Single RNA Molecules," Biophysical Journal, vol. 77:3227-3233 (1999).
Ashkenasy, Nurit et al., "Recognizing a Single Base in an Individual DNA Strand: A Step Toward DNA Sequencing in Nanopores," Angew. Chem. Int. Ed., vol. 44:1401-1404 (2005).
Ashkenasy, Nurit et al., "Single Nucleobase Sensitivity of a-Hemolysin (a-HL) Transmembrane Protein Pore: Toward Single DNA Sequencing," ACS National Meeting, vol. 45(13), Abstract No. 74 (2005).
Bayley, Hagan et al., "Stochastic sensors inspired by biology," Nature, vol. 413:226-230 (2001).
Braha, Orit et al., "Carriers versus Adapters in Stochastic Sensing," ChemPhysChem., vol. 6:889.892 (2005).

(Continued)

Primary Examiner — Stephen Kapushoc
(74) Attorney, Agent, or Firm — Nelson Mullins Riley & Scarborough LLP; Jane E. Remillard, Esq.; Christopher L. Frank

(57) ABSTRACT

The invention relates to a method of identifying an individual nucleotide, comprising (a) contacting the nucleotide with a transmembrane protein pore so that the nucleotide interacts with the pore and (b) measuring the current passing through the pore during the interaction and thereby determining the identity of the nucleotide. The invention also relates to a method of sequencing nucleic acid sequences and kits related thereto.

12 Claims, 9 Drawing Sheets

(56) References Cited

FOREIGN PATENT DOCUMENTS

| | | |
|---|---|---|
| WO | 2008/083554 A1 | 7/2008 |
| WO | 2008/102120 A1 | 8/2008 |
| WO | 2008/102121 A1 | 8/2008 |
| WO | 2008/124107 A1 | 10/2008 |
| WO | 2010/004265 A1 | 1/2010 |
| WO | 2010/034018 A2 | 3/2010 |

OTHER PUBLICATIONS

Braha, Orit et al., "Designed protein pores as components for biosensors," Chemistry & Biology, vol. 4:497-505 (1997).

Braslavsky, Ido et al., "Sequence information can be obtained from single DNA molecules," PNAS, vol. 100 (7)13960-3964 (2003).

Budanova, Natalia et al., "Heptakis(6-amino-6-deoxy)-beta-cyclodextrin as a chiral selector for the separation of anionic analyte enantiomers by capillary electrophoresis," Electresphoresis, vol. 25:2795-2800 (2004).

Chan, Eugene Y., "Advances in sequencing technology," Mutation Research. vol. 573:13-40 (2005).

Cheley, Stephen et al., "Stochastic Sensing of Nanoniolar Inositol 1,4,5-Triphosphate with an Engineered Pore," Chemistry & Biology, vol. 9:829-838 (2002).

Dapprich, Johannes, "Single-Molecule DNA Digestion by Lambda-Exonuclease," Cytometry, vol. 36:163-168 (1999).

Deamer, David W. et al., "Characterization of Nucleic Acids by Nanopore Analysis," Ac. Chem Res., vol. 35:817-825 (2002).

Deamer, David W. et al., "Nanopores and nucleic acids: prospects for ultrarapid sequencing," TIBTECH, vol. 18:147-151 (2000).

Dorre, Klaus et al., "Techniques for single molecule sequencing," Bioimaging, vol. 5:139-152 (1997).

Eliseev, Alexey V. et al., "Molecular Recognition of Nuceotides, Nucleosides, and Sugars by Aminocyclodextrins," J. Am. Chem. Soc., vol. 116:6081-6088 (1994).

Gu, Li-Qun et al., "Stochastic sensing of organic analytes by a pore-forming protein containing a molecular adapter," Nature, vol. 398:686-690 (1999).

Howorka, Stefan et al., "Kinetics of duplex formation for individual DNA strands within a single protein nanopore," PNAS, vol. 98(23):12996-13001 (2001).

Howorka, Stefan et al., "Sequence-specific detection of individual DNA strands using engineered nanopores," Nature Biotechnology, vol. 19:636-639 (2001).

Kasianowicz, John J. et al., "Characterization of individual polynucleotide molecules using a membrane channel," Proc. Natl. Acad. Sci. USA, vol. 93:13770-13773 (1996).

Khulbe, Pramod K. et al., "DNA translocation through a-hemolysin nanopores with potential application to macromolecular data storage," Journal of Applied Physics, vol. 97(104317):1-7 (2005).

Li, Jiali et al., "DNA molecules and configurations in a lid-state nanopore microscope," Nature, vol. 2:611-615 (2003).

Martínez, Javier et al., "The mRNA Cap Structure Stimulates Rate of Poly(A) Removal and Amplifies Processivity of Degradation," The Journal of Biological Chemistry, vol. 276(30):27923-27929 (2001).

Marziali, Andre et al., "New DNA Sequencing Methods," Annu. Rev. Biomed. Eng., vol. 3:195-223 (2001).

Mathé, Jérôme et al., "Orientation discrimination of a single-stranded DNA inside the a-hemolysin membrane channel," PNAS, vol. 102(35):12377-12382 (2005).

Matsuura, Shun-ichi et al., "Real-time observation of a single DNA digestion by I exonuclease under a fluorescence microscope field," Nucleic Acids Research, vol. 29(16)1-5 (2001).

Meller, Amit et al., "Rapid nanopore discrimination between single polynucleotide molecules," PNAS, vol. 97 (3):1079-1084 (2000).

Nakane, Jonathan et al., "A Nanosensor for Transmembrane Capture and Identification of Single Nucleic Acid Molecules," Biophysical Journal, vol. 87:615-621 (2004).

Nakane, Jonathan J. et al., "Nanopore sensors for nucleic acid analysis," J. Phys.: Condens. Matter, vol. 15:R1365-R1393 (2003).

Sutherland, Todd C. et al., "An analysis of mismatched duplex DNA unzipping through a bacterial nanopore," Biochem. Cell Biol., vol. 82:407-412 (2004).

Tadey, Tanya et al., "Capillary electrophoretic separation nucleotide isomers via complexation with cyclodextrin and borate," Journal of Chromatography B, vol. 657:365-372 (1994).

Tohda, Koji et al., "Channel Mimetic Sensing Membranes for Nucleotides Based on Multitopic Hydrogen Bonding," Israel Journal of Chemistry, vol. 37:267-275 (1997).

Van De Goor, Tom A., "Nanopore Detection: Threading DNA Through a Tiny Hole," PharmaGenomic, vol. 4 (3):28-30 (2004).

Wang, Hui et al., "Nanopores with a spark for single-molecule detection," Nature Biotechnology, vol. 19:622-623 (2001).

Xie, Hongzhi et al., "Single-Molecule Observation of the Catalytic Subunit of cAMP-Dependent Protein Kinase Binding to an Inhibitor Peptide," Chemistry & Biology, vol. 12:109-120 (2005).

International Preliminary Report on Patentability for Application No. PCT/GB2006/004265, dated May 20, 2008, (pp. 1-7).

U.S. Appl. No. 13/129,278, filed Aug. 26, 2011, Giovanni Maglia.
U.S. Appl. No. 13/147,171, filed Nov. 10, 2011, Ruth Moysey.
U.S. Appl. No. 13/147,159, filed Nov. 15, 2011, Brian McKeown.
U.S. Appl. No. 13/147,176, filed Nov. 18, 2011, Lakmal Jayasinghe.
U.S. Appl. No. 13/260,178, filed Jan. 17, 2012, David Stoddart.
U.S. Appl. No. 12/093,610, filed Sep. 27, 2011, Stephen Thomas Kapushoc.
U.S. Appl. No. 12/681,643, filed Mar. 8, 2013, Ruixing Li.
U.S. Appl. No. 12/681,643, filed Jul. 10, 2012, Ruixing Li.
U.S. Appl. No. 13/129,278, filed Jun. 11, 2013, Ruixing Li.
U.S. Appl. No. 13/129,278, filed Feb. 27, 2013, Ruixing Li.
U.S. Appl. No. 13/147,171, filed May 6, 2013, Nashaat T. Nashed.
U.S. Appl. No. 13/147,171, filed Jan. 3, 2013, Nashaat T. Nashed.
U.S. Appl. No. 13/147,159, filed May 28, 2013, Joseph G. Dauner.
U.S. Appl. No. 13/147,159, filed Jan. 25, 2013, Joseph G. Dauner.
U.S. Appl. No. 13/260,178, filed May 9, 2013, Robert Thomas Crow.
U.S. Appl. No. 13/260,178, filed Feb. 20, 2013, Robert Thomas Crow.

Amblard, Franck et al., "The Cu(I)-catalyzed Huisgen azide-alkyne 1,3-dipolar cycloaddition reaction in nucleotide and oligonucleotide chemistry," Chem. Rev., vol. 109(9):4207-4220 (2009).

Astier, Yann et al., "Stochastic Detection of Motor Protein-RNA Complexes by Single-Channel Current Recording," ChemPhysChem, vol. 8:2189-2194 (2007).

Astier, Yann et al., "Toward Single Molecule DNA Sequencing: Direct Identification of Ribonucleoside and Deoxyribonucleoside 5'-Monophosphates by Using an Engineered Protein Nanopore Equipped with a Molecular Adapter," J. Am. Chem. Soc., vol. 128:1705-1710 (2006).

Bayley, Hagan, "Sequencing single molecules of DNA," Current Opinion in Chemical Biology, vol. 10:628-637 (2006).

Benner, Seico et al., "Sequence-specific detection of individual DNA polymerase complexes in real time using a nanopore," Nature Nanotechnology, vol. 2:718-724 (2007).

Branton, Daniel et al., "The potential and challenges of nanopore sequencing," Nat. Biotechnol., vol. 26 (10):1146-1153 (2008).

Busam, Robert D., "Structure of *Escherichia coli* exonuclease I in complex with thymidine 5'-monophosphate," Acta Cryst., vol. D64:206-210 (2008).

Butler, Tom Z. et al., "Determination of RNA Orientation during Translocation through a Biological Nanopore," Biophysical Journal, vol. 90:190-199 (2006).

Butler, Tom Z. et al., "Single-molecule DNA detection with an engineered MspA protein nanopore," PNAS, vol. 105 (52):20647-20652 (2008).

Cheley, Stephen et al., "A functional protein pore with a 'retro' transmembrane domain," Protein Science, vol. 8:1257-1267 (1999).

Cheley, Stephen et al., "A Genetically Encoded Pore for the Stochastic Detection of a Protein Kinase," ChemBioChem, vol. 7:1923-1927 (2006).

Cheley, Stephen et al., "Spontaneous oligomerization of a staphylococcal alpha-hemolysin conformationally constrained by removal of residues that form the transmembrane beta-barrel," Protein Engineering, vol. 10 (12):1433-1443 (1997).

(56) References Cited

OTHER PUBLICATIONS

Chen, Peng et al., "Atomic Layer Deposition to Fine-Tune the Surface Properties and Diameters of Fabricated Nanopores," Nano Letters, vol. 4(7):1333-1337 (2004).
Chen, Min et al., "Outer membrane protein G: Engineering a quiet pore for biosensing," PNAS, vol. 105 (17):6272-6277 (2008).
Clarke, James et al., "Continuous base identification for single-molecule nanopore DNA sequencing," Nature Nanotechnology, vol. 4:265-270 (2009).
Cockroft, Scott L. et al., "A Single-Molecule Nanopore Device Detects DNA Polymerase Activity with Single-Nucleotide Resolution," J.Am. Chem. Soc., vol. 130:818-820 (2008).
Comai, Massimiliano et al., "Protein engineering modulates the transport properties and ion selectivity of the pores formed by staphylococcal γ-haemolysins in lipid membranes," Molecular Microbiology, vol. 44(5):1251-1267 (2002).
Eid, John et al., "Real-Time DNA Sequencing from Single Polymerase Molecules," Science, vol. 323:133-138 (2009).
Eliseev, Alexey V. et al., "Aminocyclodextrins as Selective Hosts with Several Binding Sites for Nucleotides," Angew. Chem. Int. Ed. Engl., vol. 32(9):1331-1333 (1993).
Erie, Dorothy et al., "A Dumbell-Shaped, Double-Hairpin Structure of DNA: A Thermodynamic Investigation," Biochemistry, vol. 26:7150-7159 (1987).
Flomembom, O. et al., Single stranded DNA translocation through a nanopore: A master equation approach, Physical Review E, vol. 68:041910, DOI: 10.1103/PhysRevE.68.041910, 7 pages, (2003).
Flusberg, Benjamin A. et al., "Direct detection of DNA methylation during single-molecule, real-time sequencing," Nature Methods, vol. 7(6):461-465 (2010).
Genschel, Jochen et al., "Interaction of E. coli Single-Stranded DNA Binding Protein (SSB) with Exonuclease I. The Carboxy-Terminus of SSB is the Recognition Site fo the Nuclease," Biol. Chem., vol. 381:183-192 (2000).
Gershow, Marc et al., "Recapturing and trapping single molecules with a solid-state nanopore," Nature Nanotechnology, vol. 2:775-779 (2007).
Ghosal, Sandip, "Electrokinetic-flow-induced viscous drag on a tethered DNA inside a nanopore," Physical Review E, vol. 76:061916, DOI: 10.1103/PhysRevE.76.061916, 3 pages, (2007).
Gu, Li-Qun et al., "Capture of a Single Molecule in a Nanocavity," Science, vol. 291:636-640 (2001).
Gu, Li-Qun et al., "Electroosmotic enhancement of the binding of a neutral molecule to a transmembrane pore," PNAS, vol. 100(26):15498-15503 (2003).
Gu, Li-Qun et al., "Prolonged Residence Time of a Noncovalent Molecular Adapter, beta-Cyclodextrin, within the Lumen of Mutant alpha-Hemolysin Pores," J. Gen. Physiol., vol. 118:481-493 (2001).
Gu, Li-Qun et al., "Reversal of charge selectivity in transmembrane protein pores by using noncovalent molecular adapters," PNAS, vol. 97(8):3959-3964 (2000).
Guan, Xiyun et al., "Stochastic Sensing of TNT with a Genetically Engineered Pore," ChemBioChem, vol. 6:1875-1881 (2005).
Han, Jongyoon et al., "Characterization and Optimization of an Entropic Trap for DNA Separation," Anal. Chem., vol. 74:394-401 (2002).
Han, Eugene S. et al., "RecJ exonuclease: substrates, products and interaction with SSB," Nucleic Acids Research, vol. 34(4):1084-1091 (2006).
Hein, Christopher D. et al., "Click Chemistry, a Powerful Tool for Pharmaceutical Sciences," Pharm. Res., vol. 25 (10):2216-2230 (2008).
Henrickson, Sarah E. et al., "Driven DNA Transport into an Asymmetric Nanometer-Scale Pore," Physical Review Letters, vol. 85(14):3057-3060 (2000).
Holden, Matthew A. et al., "Direct Introduction of Single Protein Channels and Pores into Lipid Bilayers," J. Am. Chem. Soc., vol. 127:6502-6503 (2005).
Holden, Matthew A. et al., "Functional Bionetworks from Nanoliter Water Droplets," J. Am. Chem. Soc., vol. 129:8650-8655 (2007).

Hornblower, Breton et al., "Single-molecule analysis of DNA-protein complexes using nanopores," Nature Methods, vol. 4(4):315-317 (2007).
Howorka, Stefan et al., "DNA Duplex Formation of Individual DNA Strands within a Single Protein Pore," Biophysical Journal, vol. 82(1, pt. 2):508a, No. 2482-Plat (2002).
Howorka, S. et al., "Improved Protocol for High-Throughput Cysteine Scanning Mutagenesis," Biotechniques, vol. 25(5):764-766 (1998).
Howarka, Stefan et al., "Probing Distance and Electrical Potential within a Protein Pore with Tethered DNA," Biophysical Journal, vol. 83:3202-3210 (2002).
Hu, Tao et al., "Theory of DNA translocation through narrow ion channels and nanopores with charged walls," Physical Review E, vol. 78:032901, DOI: 10.1103 1PhysRevE.78.032901, 3 pages, (2008).
Hwang, William L. et al., "Electrical Behavior of Droplet Interface Bilayer Networks: Experimental Analysis and Modeling," J. Am. Chem. Soc., vol. 129:11854-11864 (2007).
Jayasinghe, Lakmal et al., "The leukocidin pore: Evidence for an octamer with four LukF subunits and four LukS subunits alternating around a central axis," Protein Science, vol. 14:2550-2561 (2005).
Jung, Yuni et al., "The Internal Cavity of the Staphylococcal alpha-Hemolysin Pore Accommodates ~175 Exogenous Amino Acid Residues," Biochemistry, vol. 44(25):8919-8929 (2005).
Kalisch, Bernd W. et al., "Covalently linked sequencing primer linkers (splinkers) for sequence analysis of restriction fragments (Recombinant DNA; hairpin ligation; synthetic oligodeoxynucleotides; dideoxynucleotides)," Gene, vol. 44:263-270 (1986).
Kang, Xiao-feng et al., "Single Protein Pores Containing Molecular Adapters at High Temperatures," Angew. Chem. Int. Ed., vol. 44:1495-1499 (2005).
Kocalka, Petr et al., "Rapid and Efficient DNA Strand Cross-Linking by Click Chemistry," ChemBioChem, vol. 9:1280-1285 (2008).
Kolb, Hartmuth C. et al., "Click Chemistry: Diverse Chemical Function from a Few Good Reactions," Angew. Chem. Int. Ed., vol. 40:2004-2021 (2001).
Kovall, Rhett et al., "Toroidal Structure of Lambda-Exonuclease," Science, vol. 277:1824-1827 (1997).
Lovett, Susan T. et al., "Identification and purification of a single-stranded-DNA-specific exonuclease encoded by the recJ gene of Escherichia coli," Proc. Natl. Acad. Sci. USA, vol. 86:2627-2631 (1989).
Lovrinovic, Marina et al., "Rapid synthesis of DNA-cysteine conjugates for expressed protein ligation," Biochemical and Biophysical Research Communications, vol. 335:943-948 (2005).
Luo, Kaifu et al., "Influence of Polymer-Pore Interactions on Translocation," Physical Review Letters, vol. 99:148102, DOI: 10.1103/PhysRev Lett. 99.148102, 4 pages, (2007).
Lutz, Jean-Francois et al., "Efficient construction of therapeutics, bioconjugates, biomaterials and bioactive surfaces using azide-alkyne 'click' chemistry," Advanced Drug Delivery Reviews, vol. 60:958-970 (2008).
Maglia, Giovanni et al., "Enhanced translocation of single DNA molecules through alpha-hemolysin nanopores by manipulation of internal charge," PNAS, vol. 105(50):19720-19725 (2008).
Martin, Hugh et al., "Nanoscale Protein Pores Modified with PAMAM Dendrimers," J. Am. Chem. Soc., vol. 129:9640-9649 (2007).
Meller, Amit, "Dynamics of polynucleotide transport through nanometre-scale pores," Journal of Physics: Condensed Matter, vol. 15:R581-R607 (2003).
Meller, Amit et al., "Single molecule measurements of DNA transport through a nanopore," Electrophoresis, vol. 23: 2583-2591 (2002).
Merzlyak, Petr G. et al., "Conductance and Ion Selectivity of a Mesoscopic Protein Nanopore Probed with Cysteine Scanning Mutagenesis," Biophysical Journal, vol. 89:3059-3070 (2005).
Mitchell, Nick et al., "Chemical Tags Facilitate the Sensing of Individual DNA Strands with Nanopores," Angew. Chem. Int. Ed., vol. 47:5565-5568 (2008).

(56) References Cited

OTHER PUBLICATIONS

Mohammad, Mohammad M. et al., "Controlling a Single Protein in a Nanopore through Electrostatic Traps," J. Am. Chem. Soc., vol. 130:4081-4088 (2008).
Mol, Clifford D. et al., "Structure and function of the multifunctional DNA-repair enzyme exonuclease III," Nature, vol. 374:381-386 (1995).
Movileanu, Llviu et al., "Detecting protein analytes that modulate transmembrane movement of a polymer chain within a single protein pore," Nature Biotechnology, vol. 18:1091-1095 (2001).
Movileanu, Liviu et al., "Location of a Construction in the Lumen of a Transmembrane Pore by Targeted Covalent Attachment of Polymer Molecules," J. Gen. Physiol., vol. 117:239-251 (2001).
Muller, Joachim et al., "DNA-directed assembly of artificial multienzyme complexes," Biochemical and Biophysical Research Communications, vol. 377:62-67 (2008).
Niemeyer, Christof M. et al., "DNA-Directed Assembly of Bienzymic Complexes from In Vivo Biotinylated NAD(P)H: FMN Oxidoreductase and Luciferase," ChemBioChem., vol. 3:242-245 (2002).
Nwe, Kido et al., "Growing Applications of 'Click Chemistry' for Bioconjugation in Comtemporary Biomedical Research," Cancer Biotherapy and Radiopharmaceuticals, vol. 24(3):289-302 (2009).
Paner, Teodoro M. et al., "Studies of DNA Dumbells. III. Theoretical Analysis of Optical Melting Curves of Dumbells with a 16 Base-Pair Duplex Stem and Tn End Loops (n=2, 3, 4, 5, 6, 8, 10, 14)," Biopolymers, vol. 32(7):881-892 (1992).
Paner, Teodoro M. et al., "Studies of DNA Dumbells. VI. Analysis of Optical Melting Curves of Dumbells with a Sixteen-Base Pair Duplex Stem and End-Loops of Variable Size and Sequence," Biopolymers, vol. 39:779-793 (1996).
Phoenix, David A. et al., "OmpF-LPP Signal Sequence Mutants with Varying Charge Hydrophobicity Ratios Provide Evidence for a Phosphatidylglycerol-Signal Sequence Interaction during Protein Translocation across the *Escherichia coli* Inner Membrane," The Journal of Biological Chemistry, vol. 268(23):17069-17073 (1993).
Purnell, Robert F. et al., "Nucleotide Identificaiton and Orientation Discrimination of DNA Homopolymers Immobilized in a Protein Nanopore," Nano Letters, vol. 8(9):3029-3034 (2008).
Sanchez-Quesada, Jorge et al., "Cyclic Peptides as Molecular Adapters for a Pore-Forming Protein," Journal of the American Chemical Society, vol. 122(48):11757-11766 (2000).
Sanchez-Quesada, Jorge et al., "Single DNA Rotaxanes of a Transmembrane Pore Protein," Angew. Chem. Int. Ed., vol. 43:3063-3067 (2004).
Sanderson, Katherine, "Standard and Pores. Could the next generation of genetic sequencing machines be built froma collection of miniscule holes?" Nature News, vol. 456(7218):23-25 (2008).
Sauer-Budge, Alexis F. et al., "Unzipping Kinetics of Double-Stranded DNA in a Nanopore," Phys. Rev. Letters, vol. 90(23):238101-1-238101-4 (2003).
Seeman, Nadrian C., "Nucleic Acid Junctions and Lattices," J. theor. Biol., vol. 99:237-247 (1982).
Seo, Tae Seok et al., "Click Chemistry to Construct Fluorescent Oligonucleotides for DNA Sequencing," J. Org. Chem., vol. 68:609-612 (2003).
Seol, Yeonee, Stretching of Homopolymeric RNA Reveals Single-Stranded Helices and Base-Stacking, Physical Review Letters, vol. 98:158103, DOI: 10.1103/PhysRevLett.98.158103, 4 pages, (2007).
Shank, Lalida P. et al., "Redesigning Channel-Forming Peptides: Amino Acid Substitutions that Enhance Rates of Supramolecular Self-Assembly and Raise Ion Transport Activity," Biophysical Journal, vol. 90:2138-2150 (2006).
Shin, Seong-Ho et al., "Kinetics of a Reversible Covalent-Bond-Forming Reaction Observed at the Single-Molecule Level," Angew. Chem. Int. Ed., vol. 41(19):3707-3709 (2002).
Smeets, Ralph M.M. et al., "Salt Dependence of Ion Transport and DNA Translocation through Solid-State Nanopores," Nano Letters, vol. 6(1):89-95 (2006).
Song, Langzhou et al., "Structure of Staphylococcal alpha-Hemolysin, a Heptameric Transmembrane Pore," Science, vol. 274:1859-1866 (1996).
Stoddart, David et al., "Multiple base-recognition sites in a biological nanopore—two heads are better than one," Angew. Chem. Int. Ed. Engl., vol. 49(3):556-559 (2010).
Stoddart, David et al., "Single-nucleotide discrimination in immobilized DNA oligonucleotides with a biological nanopore," PNAS, vol. 106(19):7702-7707 (2009).
Thomas, Kirk R. et al., "Processivity of DNA Exonucleases," The Journal of Biological Chemistry, vol. 253(2):424-429 (1978).
Travers, Kevin J. et al., "A flexible and efficient template format for circular consensus sequencing and SNP detection," Nucleic Acids Research, vol. 38(15):e159, doi:10.1093/nar/gkq543 (2010).
Tung, Ching-Hsuan, "Preparation and Applications of Peptide-Oligonucleotide Conjugates," Bioconjugate Chemistry, vol. 11(5):605-618 (2000).
Walker, Barbara et al., "Key Residues for Membrane Binding, Oligomerization and Pore Forming Activity of Staphylococcal alpha-Hemolysin Identified by Cysteine Scanning Mutagenesis and Targeted Chemical Modification," The Journal of Biological Chemistry, vol. 270 (39):23065-23071 (1995).
Wang, Qian et al., "Bioconjugation by Copper(I)-Catalyzed Azide-Alkyne [3+2] Cycloaddition," J. Am. Chem. Soc., vol. 125:3192-3193 (2003).
Wanunu, Meni et al., "DNA Translocation Governed by Interactions with Solid-State Nanopores," Biophysical Journal, vol. 95:4716-4725 (2008).
Wemmer, David E. et al., "Preparation and melting of single strand circular DNA loops," Nucleic Acids Research, vol. 13(23):8611-8621 (1985).
Winters-Hilt, Stephen et al., "Highly Accurate Classification of Watson-Crick Basepairs on Termini of Single DNA Molecules," Biophysical Journal, vol. 84:967-976 (2003).
Wolfe, Aaron J. et al., "Catalyzing the Translocation of Polypeptides through Attractive Interactions," J. Am. Chem. Soc., vol. 129:14034-14041 (2007).
Wong, C.T.A. et al., "Polymer capture by electro-osmotic flow of oppositely charged nanopores," The Journal of Chemical Physics, vol. 126:164903-1-164903-6 (2007).
Wu, Hai-Chen et al., "Protein Nanopores with Covalently Attached Molecular Adapters," J. Am. Chem. Soc., vol. 129:16142-16148 (2007).
Yamagata, Atsushi et al., "Overexpression, purification and characterization of RecJ protein from *Thermus thermophilus* HB8 and its core domain," Nucleic Acids Research, vol. 29(22):4617-4624 (2001).
International Preliminary Report on Patentability and Written Opinion for Application No. PCT/GB2009/001679, 6 pages, dated Jan. 11, 2011.
International Search Report for Application No. PCT/GB2009/001679, 3 pages, dated Nov. 5, 2009.
International Preliminary Report on Patentability for Application No. PCT/GB2008/003372, 6 pages, dated Apr. 7, 2010.
International Search Report for Application No. PCT/GB2009/001690, 3 pages, dated Oct. 13, 2009.
International Preliminary Report on Patentability and Written Opinion for Appliction No. PCT/GB2009/001690, 9 pages, dated Jan. 11, 2011.

\* cited by examiner

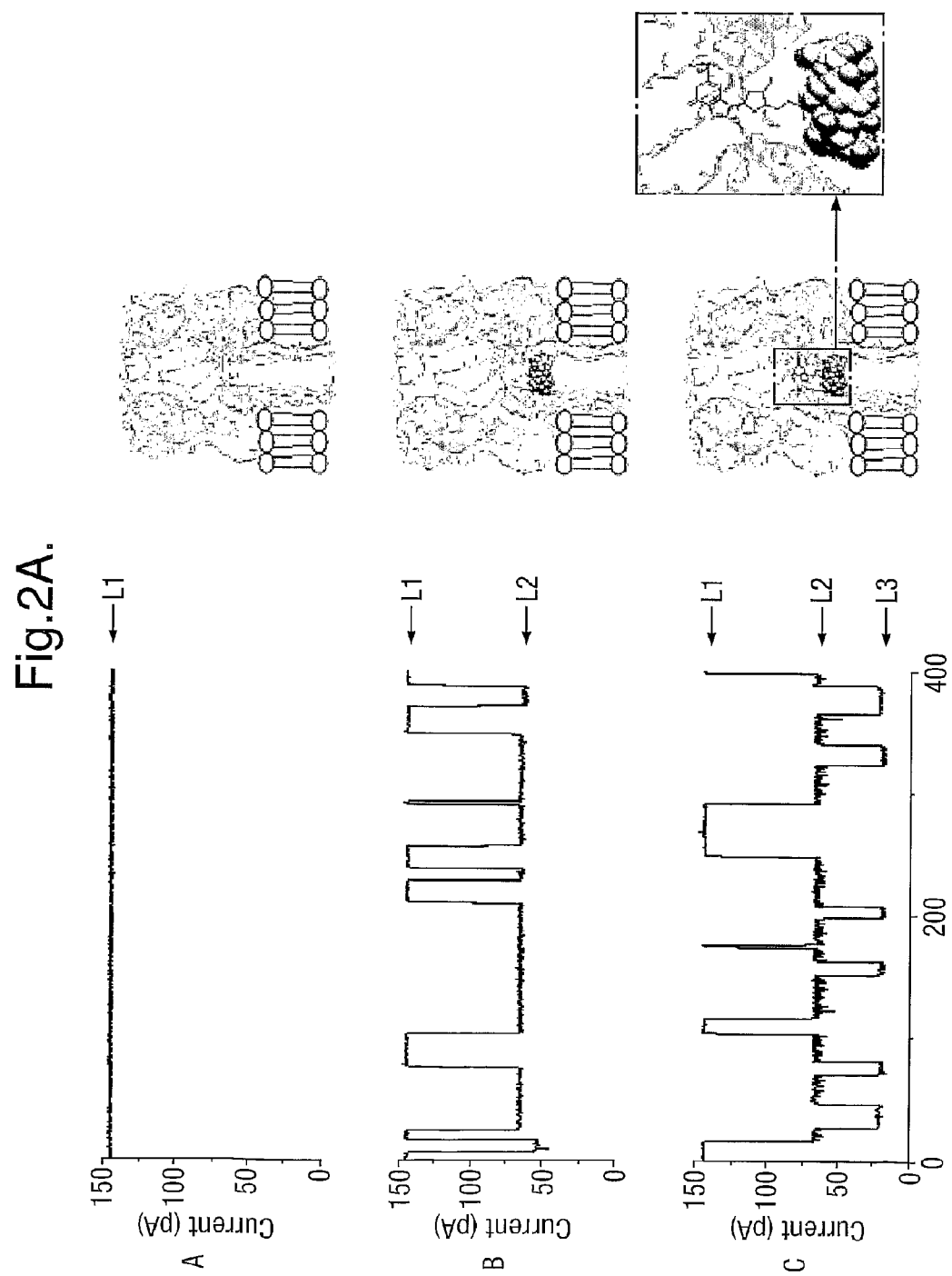

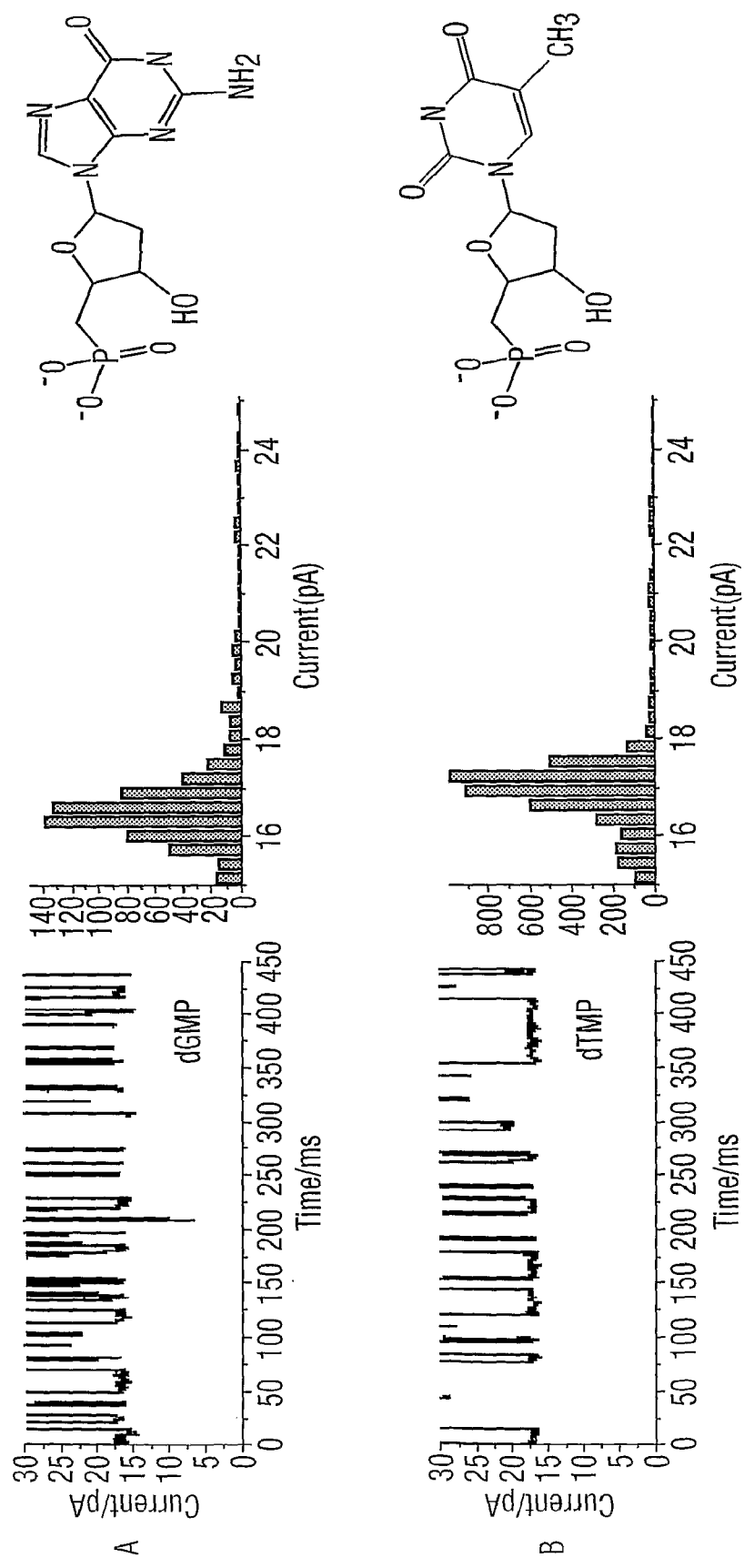

METHODS USING PORES

Related Applications

This application is a continuation of U.S. Ser. No. 12/093,610, filed on Jul. 28, 2008 (allowed), which is a 35 U.S.C. §371 national stage filing of PCT Application No. PCT/GB2006/004265 filed on Nov. 15, 2006, which claims priority to, and the benefit of, GB Application No. 0523282.2 filed on Nov. 15, 2005. The contents of the aforementioned applications are hereby incorporated by reference.

FIELD OF THE INVENTION

The invention relates to the identification of individual nucleotides and other phosphate containing moieties using transmembrane pores. In particular, the invention relates to the sequencing of target nucleic acids using transmembrane pores.

BACKGROUND OF THE INVENTION

The current method for sequencing DNA involves a number of costly reagents such as fluorescent ddXTPs, dXTPs, primers and polymerase. This method requires sophisticated equipment, which needs to be operated by a qualified technician. Also, this method is limited to sequences of less than one thousand nucleotides in length.

Other sequencing methods have been considered in order to reduce cost, simplify the method, and allow sequencing to take place out of the lab. Cycle extension, polymerase reading, exonuclease sequencing, and DNA micro-arrays are methods that have been considered (Braslaysky, I., B. Herbert, et al. (2003), *PNAS* 100(7): 3960-3964). These methods have been comprehensively reviewed (Marziali, A. and M. Akeson (2001), *Ann. Rev. Biomed. Eng.* 3: 195-223).

One potential method of sequencing DNA is based on threading a single strand of DNA through a nanopore and identifying its sequence from the variation in the ionic current flowing through the pore as the strand is threaded (Kasianowicz, J. J., E. Brandin, et al. (1996), *Proc. Natl. Acad. Sci.* 93: 13770-13773). A second potential approach is exonuclease sequencing (Chan, E. Y. (2005), *Mutat. Res.* 573: 13-40). This method involves digesting the DNA one nucleotide at a time (Dapprich, J. (1999), *Cytomet.* 36: 163-168; and Matsuura, S.-I., J. Komatsu, et al. (2001), *Nuc. Ac. Res.* 29(16): e79) and then identifying each of the released nucleotides. However, these methods require modification of the DNA before digestion or modification of the nucleotides once they have been released from the DNA by exonuclease. The development of exonuclease sequencing is currently being held back by the difficulty in identifying the nucleotides at the single molecular level as they are released by the enzyme. Investigators have tried to identify the nucleotides using fluorescent labeling with limited success.

Stochastic sensing involves placing a nanometer sized pore in an insulating lipid bilayer membrane and measuring the ionic transport through the pore. When an analyte interacts with a binding site within the pore, a change in the ionic current is detected (Braha, O., B. Walker, et al. (1997), *Chem. & Biol.* 4: 497-505; and Bayley, H. and P. S. Cremer (2001), *Nature* 413: 226-230). The extent and duration of the current block resulting from each binding event can reveal the identity of the analyte. The frequency of the binding events can reveal the analyte concentration. Various binding sites can be created within the pore by way of protein mutation, chemical modification, and by use of molecular adaptors and carriers (Gu, L.-Q., O. Braha, et al. (1999), *Nature* 398: 686-690; and Braha, O., J. Webb, et al. (2005), *Chem. Phys. Chem.* 6: 889-892).

SUMMARY OF THE INVENTION

It has been surprisingly demonstrated that individual nucleotides can be identified at the single molecule level from their current amplitude when they interact with a transmembrane pore. Hence, stochastic sensing may be used to identify individual nucleotides and to sequence nucleic acid sequences via exonuclease sequencing.

Accordingly, the invention provides a method of identifying an individual nucleotide, comprising:
 (a) contacting the nucleotide with a transmembrane protein pore so that the nucleotide interacts with the pore; and
 (b) measuring the current passing through the pore during the interaction and thereby determining the identity of the nucleotide.

The invention further provides:
a method of sequencing a target nucleic acid sequence, comprising:
 (a) digesting an individual nucleotide from one end of the target sequence using a processive exonuclease;
 (b) contacting the nucleotide with a transmembrane protein pore so that the nucleotide interacts with the pore;
 (c) measuring the current passing through the pore during the interaction and thereby determining the identity of the nucleotide; and
 (d) repeating steps (a) to (c) at the same end of the nucleic acid sequence and thereby determining the sequence of the nucleic acid; and
a kit for sequencing a nucleic acid, comprising:
 a cyclodextrin; and
 a processive exonuclease.

The method of sequencing of the invention is a rapid and simple DNA sequencing method at the single molecule level. It is also a cheap method of sequencing DNA because it does not involve the use of expensive reagents, such as fluorophores.

DESCRIPTION OF THE FIGURES

FIG. 2A shows dCMP detection. A—Current trace of single (M113R)$_7$ mutant inserted in a phospholipid bilayer at +130 mV. L1 identifies the current of the unoccupied protein nanopore. B—in the presence of 40 μM am$_7$-βCD in the trans chamber. L2 indicates the current level observed when am$_7$-βCD binds temporarily inside the nanopore. C—dCMP 5 μM is now added to the cis chamber. L3 shows the current level that is observed when dCMP binds to the temporary complex (M113R)$_7$/am$_7$-βCD.

DESCRIPTION OF THE SEQUENCE LISTING

Figure 1:
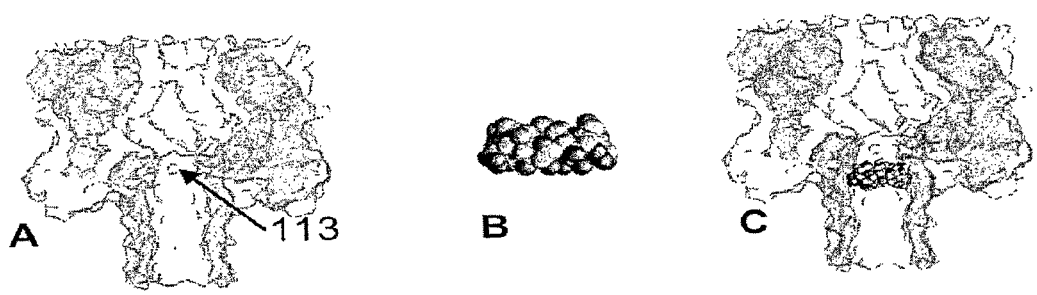
FIG. 1 shows the α-hemolysin (M113R)$_7$ mutant and heptakis-6-amino-β-cyclodextrin (am$_7$-βCD). A—sagittal cut through the α-hemolysin structure, position 113 is indicated by the arrow. B—spacefilled structure of am$_7$-βCD. C—possible interaction of am$_7$-βCD with α-hemolysin (M113R)$_7$

SEQ ID NO: 1 shows the polynucleotide sequence that encodes one subunit of α-hemolysin.
SEQ ID NO: 2 shows the amino acid sequence of one subunit of α-hemolysin.
SEQ ID NO: 3 shows the polynucleotide sequence that encodes one subunit of α-hemolysin M113H.
SEQ ID NO: 4 shows the amino acid sequence of one subunit of α-hemolysin M113H.
SEQ ID NO: 5 shows the polynucleotide sequence that encodes one subunit of α-hemolysin M113K.
SEQ ID NO: 6 shows the amino acid sequence of one subunit of α-hemolysin M113K.
SEQ ID NO: 7 shows the polynucleotide sequence that encodes one subunit of α-hemolysin M113R.
SEQ ID NO: 8 shows the amino acid sequence of one subunit of α-hemolysin M113R.
SEQ ID NO: 9 shows the amino acid sequence of lambda exonuclease. The sequence is one of three identical subunits that assemble into a trimer.

DETAILED DESCRIPTION OF THE INVENTION

Method of Identifying an Individual Nucleotide
In a first embodiment, the present invention relates to a method of identifying an individual nucleotide comprising contacting the nucleotide with a transmembrane protein pore so that the nucleotide interacts with the pore and measuring the current passing through the pore during the interaction and thereby determining the identity of the nucleotide. The invention therefore involves stochastic sensing of an individual nucleotide. The invention can be used to differentiate nucleotides of similar structure on the basis of the different effects they have on the current passing through a transmembrane protein pore. The invention can also be used to determine whether or not a particular nucleotide is present in a sample. The invention can also be used to measure the concentration of a particular nucleotide in a sample.

An individual nucleotide in accordance with the invention is a single nucleotide. An individual nucleotide is one which is not bound to another polynucleotide by a nucleotide bond. A nucleotide bond involves one of the phosphate groups of a nucleotide being bound to the sugar group of another nucleotide. An individual nucleotide is typically one which is not bound by a nucleotide bond to another polynucleotide sequence of at least 5, at least 10, at least 20, at least 50, at least 100, at least 200, at least 500, at least 1000 or at least 5000 nucleotides. For example, the individual nucleotide has been digested from a target polynucleotide sequence, such as a DNA or RNA strand. The individual nucleotide may however be bonded or attached to other chemical groups, such as fluorescent molecules or chemical groups containing radioisotopes, e.g. $^{125}$I, $^{35}$S. The types of nucleotides for identification in accordance with the invention are discussed in more detail below.

The method may be carried out using any suitable membrane/pore system in which a transmembrane protein pore is inserted into a membrane. The method is typically carried out using (i) an artificial membrane comprising a naturally-occurring or recombinant transmembrane protein pore, (ii) an isolated, naturally-occurring membrane comprising a recombinant transmembrane protein pore, (iii) an isolated, naturally-occurring membrane comprising a transmembrane protein pore or (iv) a cell expressing a naturally-occurring or recombinant transmembrane protein pore. The method is preferably carried out using an artificial membrane. The membrane may comprise other transmembrane and/or intramembrane proteins as well as other molecules in addition to the transmembrane protein pore.

The method of the invention is typically carried out in vitro.

Membrane

The membrane forms a barrier to the flow of ions and nucleotides. The membrane is preferably a lipid bilayer. Lipid bilayers suitable for use in accordance with invention can be made using methods known in the art. For example, lipid bilayer membranes can be formed using the method of Montal and Mueller (1972). The method of the invention may be carried out using lipid bilayers formed from any membrane lipid including, but not limited to, phospholipids, glycolipids, cholesterol and mixtures thereof. The lipid bilayer is preferably formed from 1,2-diphytanoyl-sn -glycero-3-phosphocholine.

Methods are known in the art for inserting pores into membranes, such as lipid bilayers. For example, the pore may be suspended in a purified form in a solution containing a lipid bilayer such that it diffuses to the lipid bilayer and is inserted by binding to the lipid bilayer and assembling into a functional state. Alternatively, the pore may be directly inserted into the membrane using the method described in M. A. Holden, H. Bayley. *J. Am. Chem. Soc.* 2005, 127, 6502-6503.

Transmembrane Protein Pore

The method of the invention is carried out using a transmembrane protein pore. A transmembrane protein pore is a polypeptide that permits ions to flow from one side of the membrane to the other along an electrochemical gradient. The pore preferably permits the nucleotide to flow from one side of the membrane to the other along an electrochemical gradient.

The pore is typically an oligomer. The pore is preferably made up of several repeating subunits. The pore is preferably pentameric or heptameric. The pore typically comprises a barrel or channel through which the ions may flow.

The barrel or channel of the pore typically comprises amino acids that facilitate interaction with the nucleotide. A pore for use in accordance with the invention typically comprises one or more positively charged amino acids, such as arginine, lysine or histidine. These positively charged amino acids are preferably located near the constriction of the barrel or channel. These amino acids typically facilitate the interaction between the pore and the nucleotide by interacting with the phosphate groups in the nucleotide or by p-cation interaction with the base in the nucleotide. The pore preferably has a ring of positively charged amino acids, such as arginine, lysine or histidine, located near the constriction of the barrel or channel. Each positively charged amino acid is typically provided by each of the pore subunits.

Suitable pores for use in accordance with the invention include, but are not limited to, α-hemolysin, porins and leukocidins.

The preferred pore for use in the invention is α-hemolysin or a variant thereof. The α-hemolysin pore is formed of seven identical subunits (heptameric). The sequence of one subunit of a-hemolysin is shown in SEQ ID NO: 2. A variant is a heptameric pore in which one or more of the seven subunits has an amino acid sequence which varies from that of SEQ ID NO: 2 and which retains pore activity. 1, 2, 3, 4, 5, 6 or 7 of the subunits in a variant α-hemolysin may have an amino acid sequence that varies from that of SEQ ID NO: 2. The seven subunits within a variant pore are typically identical but may be different.

A preferred variant of a-hemolysin has one or more positively charged amino acids, such as arginine, lysine or histidine, located near the constriction of the barrel or channel. The pore preferably has a ring of 4, 5, 6 or preferably 7 positively charged amino acids, such as arginine, lysine or histidine, located near the constriction of the barrel or channel. Each amino acid in the ring is typically provided by each of the variant subunits. Variants typically include a positively charged amino acid at position 113 of each subunit. The pore for use in the invention is preferably α-hemolysin (M113K)$_7$ which comprises seven subunits as shown in SEQ ID NO: 4 or preferably α-hemolysin (M113H)$_7$ which comprises seven subunits as shown in SEQ ID NO: 6 or most preferably α-hemolysin (M113R)$_7$ which comprises seven subunits as shown in SEQ ID NO: 8.

The variant may be a naturally-occurring variant which is expressed by an organism, for instance by a *Staphylococcus* bacterium. Variants also include non-naturally occurring variants produced by recombinant technology. Over the entire length of the amino acid sequence of SEQ ID NO: 2, a subunit of a variant will preferably be at least 50% homologous to that sequence based on amino acid identity. More preferably, the subunit polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 200 or more, for example 230, 250, 270 or 280 or more, contiguous amino acids ("hard homology").

Amino acid substitutions may be made to the amino acid sequence of SEQ ID NO: 2, for example up to 1, 2, 3, 4, 5, 10, 20 or 30 substitutions. Conservative substitutions may be made, for example, according to the following table. Amino acids in the same block in the second column and preferably in the same line in the third column may be substituted for each other:

| | | |
|---|---|---|
| NON-AROMATIC | Non-polar | G A P |
| | | I L V |
| | Polar - uncharged | C S T M |
| | | N Q |
| | Polar - charged | D E |
| | | H K R |
| AROMATIC | | H F W Y |

One or more amino acid residues of the amino acid sequence of SEQ ID NO: 2 may alternatively or additionally be deleted. Up to 1, 2, 3, 4, 5, 10, 20 or 30 residues may be deleted, or more.

Variants may include subunits made of fragments of SEQ ID NO: 2. Such fragments retain pore forming activity. Fragments may be at least 50, 100, 200 or 250 amino acids in length. Such fragments may be used to produce chimeric pores. A fragment preferably comprises the pore forming domain of SEQ ID NO: 2.

Variants include chimeric protein pores comprising fragments or portions of SEQ ID NO: 2. Chimeric protein pores are formed from subunits each comprising fragments or portions of SEQ ID NO: 2. The pore or channel part of a chimeric protein pore is typically formed by the fragments or portions of SEQ ID NO: 2.

One or more amino acids may be alternatively or additionally added to the polypeptides described above. An extension may be provided at the N-terminus or C-terminus of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention.

Standard methods in the art may be used to determine homology. For example the UWGCG Package provides the BESTFIT program which can be used to calculate homology, for example used on its default settings (Devereux et al (1984) *Nucleic Acids Research* 12, p387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSP's containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci*. USA 90: 5873-5787. One measure of similarity provided by the BLAST algorithm is the smallest sum probability (P(N)), which provides an indication of the probability by which a match between two amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

Pores used in accordance with the invention may be modified for example by the addition of histidine residues to assist their identification or purification or by the addition of a signal sequence to promote their secretion from a cell where the polypeptide does not naturally contain such a sequence. It may be desirable to provide the polypeptides in a form suitable for attachment to a solid support. For example, the pore may be attached to a solid support in order to insert the pore into the membrane.

A pore may be labelled with a revealing label. The revealing label may be any suitable label which allows the pore to be detected. Suitable labels include, but are not limited to, fluorescent molecules, radioisotopes, e.g. $^{125}$I, $^{35}$S, enzymes, antibodies, polynucleotides and linkers such as biotin.

The pore may be isolated from a pore-producing organism, such as *Staphylococcus aureus*, or made synthetically or by recombinant means. For example, the pore may be synthesized by in vitro translation transcription. The amino acid sequence of the pore may be modified to include non-naturally occurring amino acids or to increase the stability of the compound. When the pores are produced by synthetic means, such amino acids may be introduced during production. The pores may also be modified following either synthetic or recombinant production.

The pores may also be produced using D-amino acids. In such cases the amino acids will be linked in reverse sequence in the C to N orientation. This is conventional in the art for producing such proteins or peptides.

A number of side chain modifications are known in the art and may be made to the side chains of the pores. Such modifications include, for example, modifications of amino acids by reductive alkylation by reaction with an aldehyde followed by reduction with $NaBH_4$, amidination with methylacetimidate or acylation with acetic anhydride.

A recombinant transmembrane pore can be produced using standard methods known in the art. Nucleic acid sequences encoding a pore may be isolated and replicated using standard methods in the art. Nucleic acid sequences encoding a pore may be expressed in a bacterial host cell using standard techniques in the art. The pore may be introduced into a cell by in situ expression of the polypeptide from a recombinant expression vector. The expression vector optionally carries an inducible promoter to control the expression of the polypeptide.

Nucleic acid sequences encoding a pore may be isolated and replicated using standard methods in the art. Chromosomal DNA may be extracted from a pore-producing organism, such as *Staphylococcus aureus*. The gene encoding the pore may be amplified using PCR involving specific primers. The amplified sequence may then be incorporated into a recombinant replicable vector such as a cloning vector. The vector may be used to replicate the nucleic acid in a compatible host cell. Thus nucleic acid sequences encoding a pore may be made by introducing a polynucleotide encoding a pore into a replicable vector, introducing the vector into a compatible host cell, and growing the host cell under conditions which bring about replication of the vector. The vector may be recovered from the host cell. Suitable host cells for cloning of polynucleotides encoding a pore are known in the art and described in more detail below.

The nucleic acid sequence encoding a pore may be cloned into suitable expression vector. In an expression vector, the nucleic acid sequence encoding a pore is typically operably linked to a control sequence which is capable of providing for the expression of the coding sequence by the host cell. Such expression vectors can be used to express a pore.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different pore genes may be introduced into the vector.

The expression vector may then be introduced into a suitable host cell. Thus the method of the invention may be carried out on a cell produced by introducing a nucleic acid sequence encoding a pore into an expression vector, introducing the vector into a compatible bacterial host cell, and growing the host cell under conditions which bring about expression of the nucleic acid sequence encoding the pore. Alternatively, the recombinant pore produced in this manner may be isolated from the bacterial host cell and inserted into another membrane.

The vectors may be for example, plasmid, virus or phage vectors provided with an origin of replication, optionally a promoter for the expression of the said nucleic acid sequence and optionally a regulator of the promoter. The vectors may contain one or more selectable marker genes, for example a tetracycline resistance gene. Promoters and other expression regulation signals may be selected to be compatible with the host cell for which the expression vector is designed. A T7, trc, lac, ara or $\lambda_L$ promoter is typically used.

The host cell typically expresses the pore at a high level. Host cells transformed with a nucleic acid sequence encoding a pore will be chosen to be compatible with the expression vector used to transform the cell. The host cell is typically bacterial and preferably *Escherichia coli*. Any cell with a λ DE3 lysogen, for example C41 (DE3), BL21 (DE3), JM109 (DE3), B834 (DE3), TUNER, Origami and Origami B, can express a vector comprising the T7 promoter.

A pore may be produced in large scale following purification by any protein liquid chromatography system from pore-producing organisms or after recombinant expression as described above. Typical protein liquid chromatography systems include FPLC, AKTA systems, the Bio-Cad system, the Bio-Rad BioLogic system and the Gilson HPLC system. The naturally-occurring or recombinantly-produced pore may then be inserted into a naturally-occurring or artificial membrane for use in accordance with the invention.

The method of the invention may employ any one of the pores described above.

Interaction Between the Pore and Nucleotide

The nucleotide may be contacted with the pore on either side of the membrane. The nucleotide may be introduced to the pore on either side of the membrane. The nucleotide is preferably contacted with the pore on a side of the membrane that allows ions to enter the pore and flow across the membrane along an electrochemical gradient. The nucleotide is preferably contacted with a side of the membrane that allows the nucleotide to pass through the pore to the other side of the membrane. For example, the nucleotide is contacted with an end of the pore which in its native environment allows the entry of ions or small molecules, such as nucleotides, into the barrel or channel of the pore such that the ions or small molecules may pass through the pore.

The nucleotide may interact with the pore in any manner and at any site. The nucleotide preferably reversibly binds to the pore. The nucleotide more preferably reversibly binds to the barrel or the channel of the pore. The nucleotide most preferably reversibly binds to the channel or barrel of the pore as it passes through the pore across the membrane.

During the interaction between the nucleotide and the pore, the nucleotide affects the current flowing through the pore in a manner specific for that nucleotide. For example, a particular nucleotide will reduce the current flowing through the pore for a particular time period and to a particular extent. Control experiments may be carried out to determine the effect a particular nucleotide has on the current flowing through the pore. Results from carrying out the method of the invention on a test sample can then be compared with those derived from such a control experiment in order to identify a particular nucleotide in the sample or determine whether a particular nucleotide is present in the sample. The frequency at which the current flowing through the pore is affected in a manner indicative of a particular nucleotide can be used to determine the concentration of that nucleotide in the sample.

Apparatus

The method may be carried out using any apparatus that is suitable for investigating a membrane/pore system in which a transmembrane protein pore is inserted into a membrane. The method may be carried out using any apparatus that is suitable for stochastic sensing. For example, the apparatus comprises a chamber comprising an aqueous solution and a barrier that separates the chamber into two sections. The barrier has an aperture in which the membrane comprising the pore is formed. The nucleotide may be contacted with the pore by introducing the nucleotide into the chamber. The nucleotide may be introduced into either of the two sections of the chamber.

The method of the invention involves measuring the current passing through the pore during interaction with the nucleotide. Therefore the apparatus also comprises an electrical circuit capable of applying and measuring an electrical signal across the membrane and pore. The method may be carried out using a patch clamp or a voltage clamp. The method preferably involves the use of a patch clamp. The Example discloses one way of carry out a patch clamp method.

Molecular Adaptor

The transmembrane pore preferably comprises a molecular adaptor that facilitates the interaction between the pore and the nucleotide. The adaptor typically has an effect on the physical or chemical properties of the pore that improves its interaction with the nucleotide. The adaptor typically alters the charge of the barrel or channel of the pore or specifically interacts with or binds to the nucleotide thereby facilitating its interaction with the pore. The adaptor preferably interacts with one or more phosphate groups on the nucleotide or interacts with the base in the nucleotide by p-cation interaction. The adaptor may mediate the interaction between the nucleotide and the pore. For instance, the nucleotide may reversibly bind to the pore via the adaptor. Alternatively, the adaptor may interact with the nucleotide in conjunction with the pore. For instance, the nucleotide may reversibly bind to both the pore and the adaptor. The adaptor preferably constricts the barrel or channel so that it may interact with the nucleotide.

The adaptor itself may reversibly interact with the pore and may therefore move in and out of the barrel or channel of the pore. Alternatively, the adaptor may be covalently attached to the barrel or channel of the pore so that it cannot leave.

The adaptor typically has a ring of amino groups. The adaptor preferably has a ring of seven amino groups. This ring of amino groups may interact with the nucleotide in combination with a ring of positively charged amino acids in the constriction of the barrel or channel of the pore.

One suitable adaptor is cyclodextrin. The adaptor is preferably heptakis-6-amino-β-cyclodextrin ($am_7$-β-CD).

Nucleotide

The method of the invention may be used to identify any nucleotide. The nucleotide can be naturally-occuring or artificial. A nucleotide typically contains a nucleobase, a sugar and at least one phosphate group. The nucleobase is typically heterocyclic. Suitable nucleobases include purines and pyrimidines and more specifically adenine, guanine, thymine, uracil and cytosine. The sugar is typically a pentose sugar. Suitable sugars include, but are not limited to, ribose and deoxyribose. The nucleotide is typically a ribonucleotide or deoxyribonucleotide. The nucleotide typically contains a monophosphate, diphosphate or triphosphate.

Suitable nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monosphosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The nucleotide is preferably AMP, TMP, GMP, UMP, dAMP, dTMP, dGMP or dCMP.

The nucleotide may be derived from the digestion of a nucleic acid sequence such as ribonucleic acid (RNA) or deoxyribonucleic acid. Individual nucleotides from a single nucleic acid sequence may be contacted with the pore in a sequential manner in order to sequence the whole or part of the nucleic acid. Sequencing nucleic acids in accordance with the second embodiment of the invention is discussed in more detail below.

The nucleotide is typically unmodified, such as when the nucleotide is derived from the digestion of a nucleic acid sequence. Alternatively, the nucleotide may be modified or damaged. The nucleotide is typically methylated. The nucleotide may be labelled with a revealing label. The revealing label may be any suitable label which allows the nucleotide to be detected. Suitable labels include fluorescent molecules, radioisotopes, e.g. $^{125}$I, $^{35}$S, and linkers such as biotin.

The nucleotide is typically present in any suitable biological sample. The invention is typically carried out on a sample that is known to contain or suspected of containing one or more nucleotides. The invention may be carried out on a sample that contains one or more nucleotides whose identity is unknown. Alternatively, the invention may be carried out on a sample to confirm the identity of one or more nucleotides whose presence in the sample is known or expected. The invention may be carried out in vitro on a sample obtained from or extracted from any organism or microorganism. The organism or microorganism is typically prokaryotic or eukaryotic and typically belongs to one the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs.

The sample is typically processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C.

Conditions

The method of the invention involves the measuring of a current passing through the pore during interaction with the nucleotide. Suitable conditions for measuring ionic currents through transmembrane protein pores are known in the art and disclosed in the Example. The method is carried out with a voltage applied across the membrane and pore. The voltage used is typically from +50 mV to +200 mV. The voltage used is preferably from +70 mV to +150 mV, from +85 mV to +145 mV or from +100 mV to +140 mV. The voltage used is preferably about +130 mV for deoxy-ribo nucleotides 5' monophosphate, such as dAMP, dTMP, dGMP and dCMP, and +110 mV for ribo nucleotides 5' monophosphate, such as AMP, TMP, GMP and UMP.

The method is carried out in the presence of any alkali metal chloride salt. In the exemplary apparatus discussed above, the salt is present in the aqueous solution in the chamber. Potassium chloride (KCl), sodium chloride (NaCl) or caesium chloride (CsCl) is typically used. KCl is preferred. The salt concentration is typically from 0.1 to 2M, from 0.3 to 1.9M, from 0.5 to 1.8M, from 0.7 to 1.7M, from 0.9 to 1.6M or from 1M to 1.4M. The salt concentration is preferably about 1M.

The method is typically carried out in the presence of a buffer. In the exemplary apparatus discussed above, the buffer is present in the aqueous solution in the chamber. Any buffer may be used in the method of the invention. One suitable buffer is Tris-HCl buffer. The method is typically carried out at a pH of from 7.5 to 12.0, from 7.6 to 11.0, from 7.7 to 10.0, from 7.8 to 9.5, from 8.0 to 9.0 or from 8.0 to 8.5. The pH used is preferably about 8.0.

The method is typically carried out at from 14° C. to 100° C., from 15° C. to 90° C., from 16° C. to 80° C., from 17° C. to 70° C., from 18° C. to 60° C., 19° C. to 50° C., or from 20° C. to 40° C. The method is preferably carried out at room temperature.

The method is preferably carried out at +130 mV at pH 8.0, 1M KCl for deoxy-ribo nucleotides 5' monophosphate, such as dAMP, dTMP, dGMP and dCMP, and at +110 mV at pH 8.0, 1M KCl for ribo nucleotides 5' monophosphate, such as AMP, TMP, GMP and UMP.

Method of Sequencing Nucleic Acids

In a second embodiment, the invention relates to a method of sequencing a target nucleic acid sequence, comprising (a) digesting an individual nucleotide from one end of the target sequence using a processive exonuclease; (b) contacting the nucleotide with a transmembrane protein pore so that the nucleotide interacts with the pore; (c) measuring the current passing through the pore during the interaction and thereby determining the identity of the nucleotide; and (d) repeating steps (a) to (c) at the same end of the nucleic acid sequence and thereby determining the sequence of the nucleic acid. Hence, the second embodiment involves stochastic sensing of each single nucleotide of a nucleic acid sequence in a successive manner in order to sequence the nucleic acid. The whole or only part of the nucleic acid may be sequenced using the method of the second embodiment. The nucleic acid can be naturally-occuring or artificial. For instance, the method of the second embodiment may be used to verify the sequence of a manufactured oligonucleotide. The method of the second embodiment is typically carried out in vitro.

Steps (b) and (c) of the method of the second embodiment are generally identical to the steps carried out in the method of the first embodiment discussed above. All of the discussion above concerning the first embodiment, and in particular concerning the membranes, apparatus, pores, molecular adaptors, nucleotides and conditions that may be used in the first embodiment, equally applies to the second embodiment. The nucleic acid in the second embodiment is typically present in any biological sample as discussed above for the first embodiment. The method of the second embodiment may be carried out on a sample which contains one or more nucleic acids whose sequence is unknown. Alternatively the method of the second embodiment may be carried out on a sample to confirm the identity of nucleic acids whose presence in the sample is known or is expected. The nucleic acid sequence is typically amplified prior to being sequenced using the method of the second embodiment.

Processive Exonuclease

The method of the second embodiment involves contacting the nucleic acid sequence with a processive exonuclease to release individual nucleotides from one end of the nucleic acid. Processive exonucleases are enzymes that typically latch onto one end of a nucleic acid sequence and digest the sequence one nucleotide at a time from that end. The processive exonuclease can digest the nucleic acid in the 5' to 3' direction or 3' to 5' direction. The end of the nucleic acid to which the processive exonuclease binds is typically determined through the choice of enzyme used and/or using methods known in the art. Hydroxyl groups or cap structures at either end of the nucleic acid sequence may typically be used to prevent or facilitate the binding of the processive exonuclease to a particular end of the nucleic acid sequence.

Any processive exonuclease enzyme may be used in the method of the invention. The preferred enzyme for use in the method of the invention is lambda exonuclease. The sequence of one subunit of lambda exonuclease is shown in SEQ ID NO: 9. Three identical subunits interact to form a trimer exonuclease. Variants of lambda exonuclease are enzymes formed of polypeptide subunits which have an amino acid sequence which varies from that of SEQ ID NO: 9 and which retain processive exonuclease activity. The variants may vary from SEQ ID NO: 9 in the same manner and to the same extent as discussed for variants of SEQ ID NO: 2 above. A variant preferably comprises the domains responsible for binding to the nucleic acid and for digesting the nucleic acid (catalytic domain). A variant preferably has a reduced rate of enzyme activity and/or higher salt tolerance compared to the wild-type enzyme. The processive exonuclease may be produced using any of the methods discussed above for the production of transmembrane protein pores.

The method of the second embodiment involves contacting the nucleic acid sequence with the processive exonuclease so that the nucleotides are digested from the end of the nucleic acid at a rate that allows identification of each individual nucleotide in accordance with the first embodiment of the invention. Methods for doing this are well known in the art. For example, Edman degradation is used to successively digest single amino acids from the end of polypeptide such that they may be identified using High Performance Liquid Chromatography (HPLC). A homologous method may be used in the present invention.

The processive exonuclease is preferably covalently attached to the transmembrane protein pore. Methods for covalently attaching the processive exonuclease to the pore are well known in the art.

The rate at which the processive exonuclease must function in the method of the second embodiment is typically slower than the optimal rate of a wild-type processive exonuclease. A suitable rate of activity of the processive exonuclease in the method of the second embodiment involves digestion of from 0.5 to 1000 nucleotides per second, from 0.6 to 500 nucleotides per second, 0.7 to 200 nucleotides per second, from 0.8 to 100 nucleotides per second, from 0.9 to 50 nucleotides per second or 1 to 20 or 10 nucleotides per second. The rate is preferably 1, 10, 100, 500 or 1000 nucleotides per second. A suitable rate of processive exonuclease activity can be achieved in various ways. For example, variant processive exonucleases with a reduced optimal rate of activity may be used in accordance with the invention.

The activity of processive exonucleases is typically pH dependent such that their activity falls as pH is reduced. Hence, the method of the second embodiment is typically carried out at a pH of from 7.5 to 8.0 or from 7.7 to 8.0. The pH used is preferably about 8.0.

The rate of activity of processive exonucleases typically falls as salt concentration rises. However, very high salt concentrations typically have a detrimental effect on the activity of the enzyme. Another way of limiting the rate of the enzyme is to carry out the method of the second embodiment at a salt concentration that reduces the rate of the activity of the enzyme without adversely affecting its activity. For example, the method of the second embodiment may be carried out at a salt concentration of from 0.5 to 1M. The salt concentration is preferably about 1M.

Kits

In a third embodiment, the invention also relates to kits that may be used to carry out the second embodiment of the invention. The kits are therefore suitable for sequencing nucleic acids. The kits comprises a cyclodextrin and a processive exonuclease. The cyclodextrin is preferably heptakis-6-amino-β-cyclodextrin. The processive exonuclease may be any of those discussed above with reference to the second embodiment. The kit preferably further comprises a transmembrane protein pore. The pore may be any of those discussed above with reference to the first embodiment.

The kit may additionally comprise one or more other reagents or instruments which enable any of the embodiments of the method mentioned above to be carried out. Such reagents or instruments include one or more of the following: suitable buffer(s) (aqueous solutions), means to obtain a sample from a subject (such as a vessel or an instrument comprising a needle), means to amplify nucleic acid sequences, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

The following Example illustrates the invention:

EXAMPLE

In order to bring the size of the ionic conducting path of the α-hemolysin (M113R)$_7$ mutant (FIG. 1A) closer to the size of the nucleotide to be detected, the diameter of the nanopore was reduced by fitting a cyclodextrin near the constriction of the pore. The heptakis-6-amino-β-cyclodextrin (am$_7$-βCD) (FIG. 1B), which has seven amino groups in the primary positions, was used. When the cyclodextrin is inside the pore (FIG. 1C), in conjunction with the seven arginines in position 113 on the protein mutant, one ring of seven amino groups on one side, and a second ring of seven arginine groups are present within a short distance from each other in the narrowest area of the passage through the pore. This amino/arginine ring structure has the property of binding phosphate groups reversibly thus immobilising the XMP and dXMP in the pore for 5 to 30 ms. These binding events are clearly detectable through the resulting change in current amplitude.

1. Material and Methods

α-hemolysin mutant (M113R)$_7$ was expressed and purified as previously described (Cheley, S., L.-Q. Gu, et al. (2002), Chem. & Biol. 9: 829-838).

Chemicals 1,2-diphytanoyl-sn-glycero-3-phosphocholine from Avanti Polar Lipids Inc. Pentane was purchased from JT Baker, and hexadecane 99+% from Sigma-Aldrich. Heptakis (6-deoxy-6-amino)-f3-cyclodextrin.HCl >99% was purchased from CYCLOLAB Ltd Budapest, Hungary. 2-deoxy-guanosine 5' monophosphate sodium salt 99% was purchased from Acros, 2-deoxy-cytosine 5' monophosphate di-sodium salt >95%, 2-deoxy-thymidine 5' monophosphate di-sodium salt >97%, and 2-deoxy-adenosine 5' monophosphate di-sodium salt >95% from Fluka. Uridine 5' monophosphate di-sodium salt 99%, and cytosine 5' monophosphate acid >98% were bought from Fluka. Adenosine 5' monophosphate acid 99%, and guanosine 5' monophosphate di-sodium salt 97% were purchased from Acros. Trizma Base 99.9% was purchased from Sigma-Aldrich, and concentrated HCl analytical reagent grade from Fisher Scientific. Potassium chloride 99%, and sodium chloride 99.9% were purchased from Sigma-Aldrich. Potassium bromide 99.5% and cesium chloride 99% were purchased from Fluka.

Equipment

A patch clamp amplifier Axopatch 200B from Axon instruments was used with a computer equipped with a Digidata 1200 A/D converter (Axon instruments). A Teflon chamber was used. Data was collected in pClamp 9.2, and analyzed in Clampfit 9.0. Plots and graphs were obtained with Microcal Origin 6.0, and integration were run on a personal calculator.

Experimental Conditions

Lipid bilayer membranes were formed from 1,2-diphytanoyl-sn-glycero-3-phosphocholine by the method of Montal and Mueller (1972), on 100-150 µm diameter orifice in a 20 µm polycarbonate film (20 µm thickness from Goodfellow, Malvern PA) separating the trans and the cis chamber. The cis side of the chamber was at ground, and the trans side of the chamber was connected to the head stage. The potential refers to the potential value of the trans side electrode. The adaptor molecule was added to the trans side, the α-hemolysin mutant and the analyte molecules were added to the cis side. dXMP experiments were carried out at +130 mV, XMP experiments at +110 mV. All experiments reported here were obtained at pH 8.0 Tris-HCl 25 mM in 1 M KCl. Fresh aliquots of nucleotide solution were used everyday. Experiments were carried out at room temperature 22.5+/−2° C. unless stated otherwise.

Figure 2B:
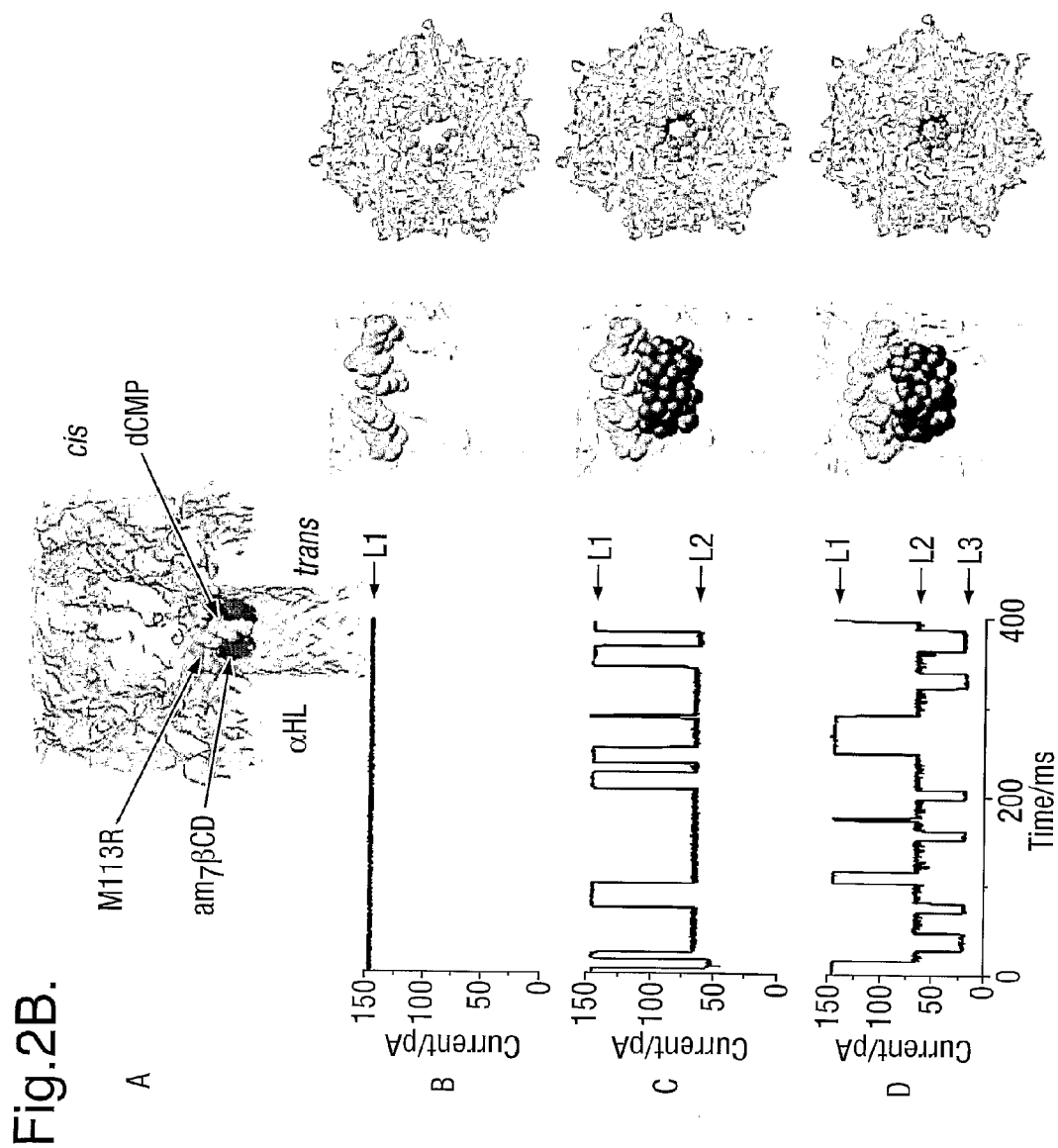
FIG. 2B shows the nteraction of the α-hemolysin (αHL) pore with heptakis-(6-deoxy-6-amino)-β-cyclodextrin (am$_7$βCD) and dCMP. A—Model of the heptameric αHL pore (7AHL), in which Met-113 has been substituted with Arg. A model of am$_7$βCD in cross-section generated in ChemDraw Ultra has been positioned manually at van der Waals distances from the Arg side chains, which block the passage of the cyclodextrin when it enters the pore from the trans side. When am$_7$βCD is present inside the pore, two rings of positive charge, one ring of seven primary amino groups contributed by the cyclodextrin, and a second ring of seven arginine side-chains, are separated by ~10 Å. Aminocyclodextrins have previously been shown to bind nucleoside monophosphates with the phosphate group in an ionic interaction with the protonated amino groups. It is possible that the overall stability of such complexes is enhanced by p-cation interactions between the nucleotide bases and the Arg side chains. The dCMP molecule is positioned so that the phosphate group interacts with the protonated amines of am$_7$βCD and the cytosine ring interacts with the guanidinium groups of the Arg side chains. B—Current trace from a single (M113R)$_7$ pore at +130 mV. L1 identifies the current flowing through the unoccupied protein nanopore, which is shown as a model on the right. C—Current trace after the addition of 40 µM am$_7$βCD to the trans chamber. L2 indicates the current level observed when am$_7$βCD is bound inside the nanopore. D—Current trace after the addition of 5 µM dCMP to the cis chamber. L3 shows the current level that is observed when dCMP binds to the (M113R)$_7$•am$_7$βCD complex.

2. Results 2-deoxy-nucleotide 5' Monophosphates Partially Block Homoheptameric Pores Formed by (M113R)$_7$/heptakis 6 amino β-cyclodextrin Single-channel recordings were carried out on the homoheptameric pores formed from αHL-M113R with am$_7$-βCD applied from the trans side (FIGS. 2A and 2B). In the absence of am$_7$-βCD, the pore remained permanently open (FIGS. 2A and 2B, B) with a unitary current (L1) of 145±5 pA (+130 mV) in 1M KCl in pH 8.0 Tris-HCl 25 mM buffer. The addition of 40 µM am$_7$-βCD in the trans chamber alone leads to reversible blocking events to a current level of 65±5 pA (L2 in FIG. 2A, B and FIG. 2B, C). Upon addition of 5 µM dCMP to the cis chamber, a third current level is observed at 22±1 pA (L3 in FIG. 2A, C and FIG. 2B, D) originating from current level L2. L3 represents the binding of dCMP to the complex of (M113R)$_7$ with am$_7$-βCD. Addition of dXMP at up to 300 µM to the trans instead of the cis side of the chamber did not lead to any alteration of the cyclodextrin binding conductance states (not shown).

In the experimental conditions described above, current blocking events due to cyclodextrin binding were observed when unmodified β-cyclodextrin was added to the trans chamber (40 µM) in the presence of a αHL-M113R single nanopore. However, no further current blocking events were observed, when dXMPs (up to 300 µM) were added either to the trans or the cis chamber (not shown).

In the absence of am$_7$-βCD in the trans chamber, blocking events (<1 ms) were observed when minimum concentrations of 300 µM dGMP or dTMP were added to the cis chamber (not shown). These events are not observed over the timescale of the experiment at 5 µM dXMP or XMP.

Adding am$_7$-βCD in the trans chamber while measuring the current through a wild type α-HL single channel led to cyclodextrin binding events, but no further alterations of the current were observed when adding dXMP to either the cis or the trans chamber.

Figure 3:
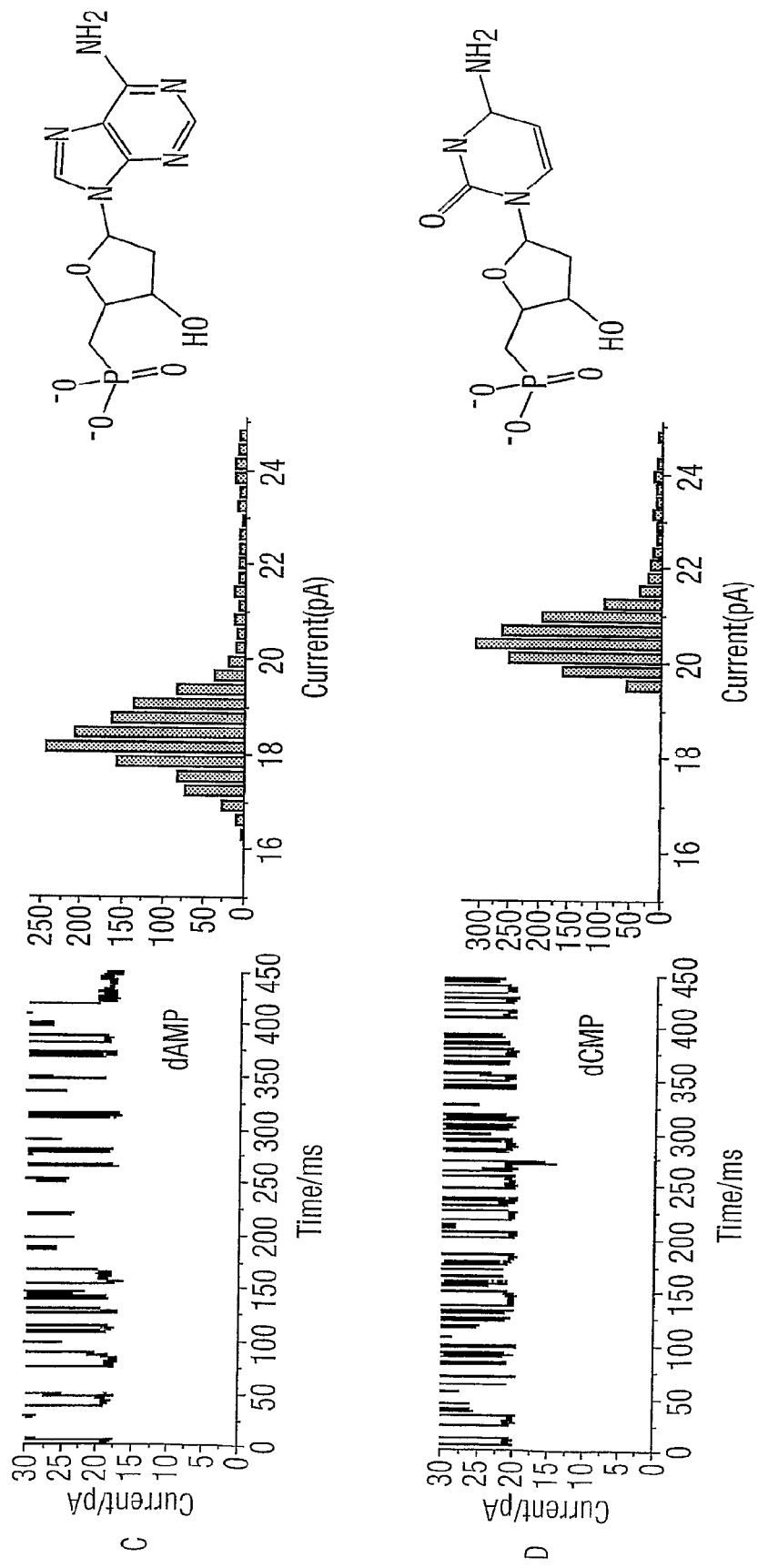
FIG. 3 shows dXMP current amplitudes. Current trace of single (M113R)$_7$ pore inserted in a phospholipid bilayer, at +130 mV potential. 40 µM am$_7$-βCD is present in the trans chamber. A—dGMP 5 µM is added to the cis chamber. The all points histogram of the current trace is shown on the right together with the structures of dGMP, dTMP (B), dAMP (C), and dCMP (D).

2-deoxy-nucleotide 5' Monophosphate can be Identified from the Amplitude of the Partial Block of Homoheptameric Pores Formed by (M113R)$_7$/heptakis 6 amino β-cyclodextrin The partial block of the transient complex (M113R)$_7$/am$_7$-βCD differed in amplitude depending on which dXMP was added to the cis chamber (FIG. 3). Addition of dGMP (5 µM) to the cis side displayed an average blocking to a current level of 16 pA (FIG. 3A). The all points amplitude histogram of the trace shown in FIG. 3A is shown to the right of the trace together with the structure of dGMP. The other nucleotides all display different amplitudes as shown in FIG. 3B for dTMP, 3C for dAMP, and 3D for dCMP. Out of the four dXMP, dGMP blocks the most current.

The current amplitudes from independent experiments displayed some variations that originated from individualities of the protein nanopore. The average current, at +130 mV, for a (M113R)$_7$ is 139 pA, but some channels display currents as high as 147 pA and as low as 131 pA. Therefore, to compare current traces current traces were normalized from different experiments between 0 current and the (M113R)$_7$/am$_7$-βCD current level set to 65 pA. The dwell time ($\tau_{off}$) of each dXMP was calculated over 500 events from each of 3 independent experiments (Table 1).

TABLE 1

Dwell time in ms of dGMP, dTMP, dAMP, and dCMP averaged from three independent measurements.

|  | dGMP | dTMP | dAMP | dCMP |
|---|---|---|---|---|
| $\tau_{off}$(ms) | 9.8 ± 0.2 | 19.8 ± 0.8 | 7.1 ± 0.2 | 10.5 ± 0.4 |

Cyclodextrin Current Levels

Figure 4:
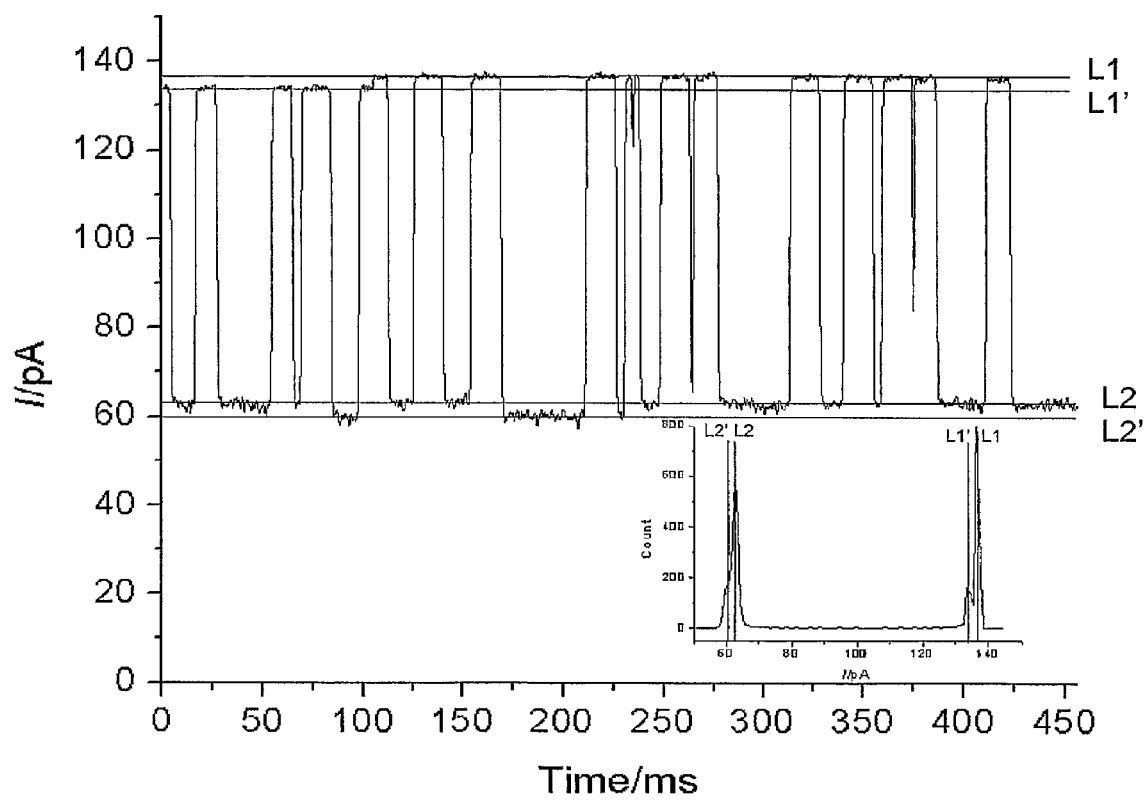
FIG. 4 shows cyclodextrin current levels. Current trace of single (M113R)$_7$ mutant inserted in a phospholipid bilayer with 40 µM am$_7$-βCD present in the trans chamber at +130 mV. L1 and L1' indicate two current levels of the unoccupied nanopore, and L2 and L2' show two current levels resulting from the binding of am$_7$-βCD to (M113R)$_7$. The insert shows the amplitude histogram of the current trace with the peaks corresponding to the current levels L1, L1', L2, and L2'.

At pH 8.0, the mutant (M113R)$_7$ exhibits two current levels L1/L1' when the protein channel is unoccupied (FIG. 4). The cyclodextrin adapter can bind to the protein regardless of which current level L1/L1' the protein is in.

Two current levels are observed when recording the current level of the (M113R)$_7$ nanopore (FIG. 4). L1 is the main current level, as shown in the insert of FIG. 4. The binding of am$_7$-βCD to the nanopore leads to two current levels represented by L2 and L2' (three levels are observed at pH 7.5, not shown). The binding of am$_7$-βCD to the protein nanopore occurs independently of current level L1 or L1'. L2 is the main conductance level observed when am$_7$-βCD is bound to (M113R)$_7$ and it originates from both L1 and L1' conductance levels of the empty nanopore with no apparent correlation. The current level L2' observed when am$_7$-βCD is bound to (M113R)$_7$ accounts for less than 15% of the conductance when the cyclodextrin adapter is bound (see insert FIG. 4).

Figure 5:
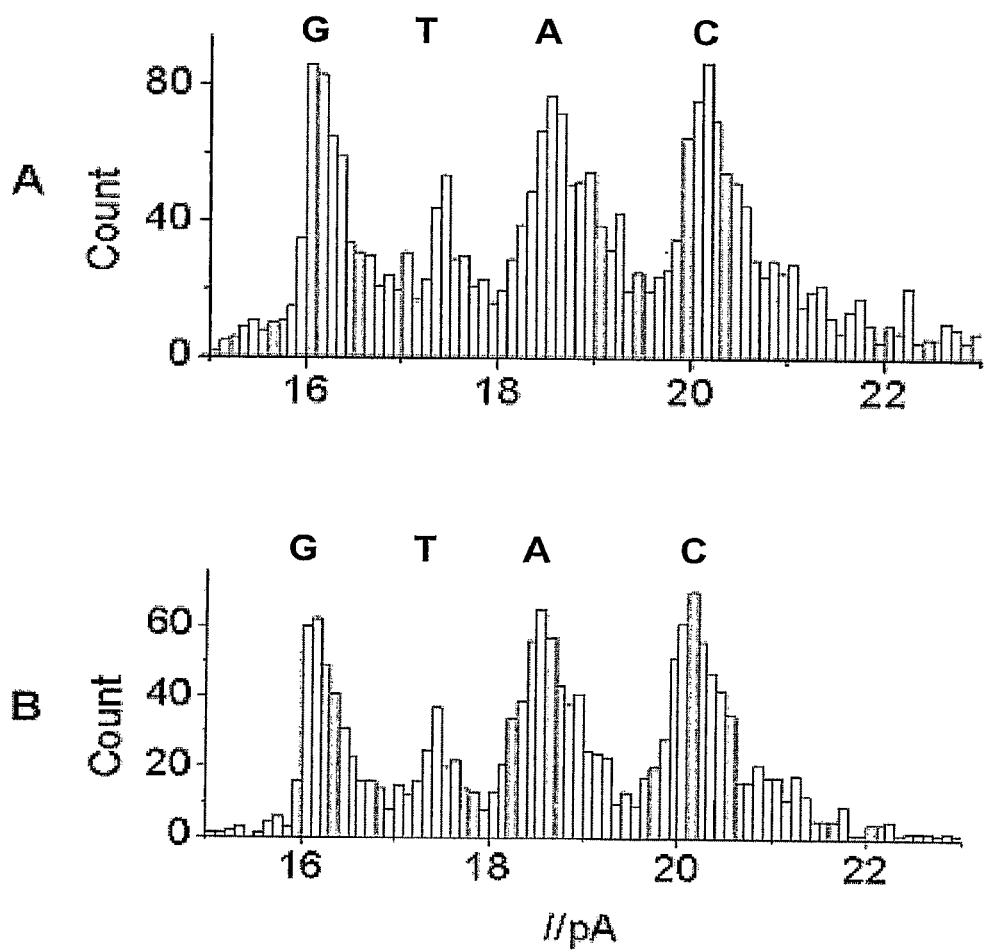
FIG. 5 shows single event analysis. A shows a single event analysis histogram of the L3 current level from all four dXMP in the same solution. B shows a single event analysis histogram of L3 originating from L2 only. 5 µM of dGMP, dAMP, dCMP, and 10 µM of dTMP are present in the cis chamber.

The nucleotide binding events sometimes vary in amplitude as a result of which current level L2 and L2' they originate from. A 0.5 pA shift was observed depending on which of L2 or L2' the dXMP binding event originates from (not shown). It leads to an increased overlap of the nucleotide binding event histogram (FIG. 5).

It is possible to analyze manually each recording in order to remove each analyte binding event stemming from the bound cyclodextrin current level L2' described in FIG. 3. FIG. 5 shows the difference between the single event analysis histogram obtained from an unmodified dXMP detection current recording (FIG. 5A), and the same recording where analyte binding events stemming off level L2' (FIG. 4) have been removed. The two histograms display the same four peaks corresponding to dGMP, dTMP, dAMP, and dCMP. The amplitude of the peaks in FIG. 5A is larger than in 5B because the analyte binding events stemming off L2' have been removed, therefore the histogram originates from fewer events. The separation between each peak seems better in 5B than in 5A. However, removing these events from the recording did not yield a complete separation of each peak (FIG. 5B). As a result, the cyclodextrin current levels L2 and L2' shown in FIG. 4 were not taken into account in the single event analysis histograms, and resulting statistics reported hereafter.

2-deoxy Nucleotide 5' Monophosphates can be Identified from the Amplitude of the Partial Block of Homoheptameric Pores Formed by the Transient Complex (M113R)$_7$/Heptakis 6 Amino β-Cyclodextrin The partial block of (M113R)$_7$/am$_7$-βCD pores proved to differ in amplitude depending on which dXMP was added to the cis chamber. The different amplitudes could be resolved when dGMP, dTMP, dAMP, and dCMP were added to the cis chamber simultaneously (FIG. 5).

FIG. 6A shows the current amplitude for a mixed solution of all 4 nucleotides from a single experiment. Colored bands are superimposed onto the recorded current trace in order to illustrate the amplitude distribution of each dXMP. FIG. 6B shows an amplitude histogram of a current trace of 8000 events assumed to be the amplitude distribution generated by each nucleotide. The amplitude histogram is superimposed with Gaussian distributions. The fit is obtained from the peak current value given by this experiment as the distribution mean value and the σ value that was obtained from fitting and averaging the distribution of each nucleotide independently (Table 2). From fitting the current traces with Gaussian distributions, the probabilities of identification for each nucleotide was established.

Statistical Methods

Current traces of (M113R)$_7$ in the presence of am$_7$-βCD on the trans side and one of the analyte nucleotides on the cis side were digitally filtered at 300 Hz (low pass Gaussian filter), and an all points amplitude histogram was constructed. These histograms display a large peak corresponding to the current amplitude that is observed when the am$_7$-βCD binds to the (M113R)$_7$ α-hemolysin mutant(corresponding to L2 in FIG. 1). This current amplitude varies between protein channels within 5% from one experiment to another. For this reason, the all points amplitude histograms were normalised between 0 current, and the main cyclodextrin peak set at 65 pA. In the normalised histogram, the nucleotide peak was fitted to a Gaussian distribution. The mean and sigma (σ) values of the same nucleotide were averaged from at least 3 independent experiments each containing 1000 events (values listed in Table 2).

TABLE 2

Average values of the distributions of each nucleotide from three independent experiments all normalised between 0 and 65 pA.

| | Average |
|---|---|
| G | 16.0, σ = 0.64 |
| T | 17.4, σ = 0.41 |
| A | 18.4, σ = 0.54 |
| C | 20.0, σ = 0.51 |

The probabilities for the reading of each base were determined from experiments with all 4 nucleotides present simultaneously over at least 3000 nucleotide binding events in each trace. The traces were filtered (300 Hz low pass Gaussian digital filter) and normalised between 0 and the cyclodextrin peak at 65 pA as described above for the individual nucleotide experiments. The peak values of each nucleotide were averaged from 5 independent experiments (Table 3).

TABLE 3

Peak values of each nucleotide where all 4 nucleotides are present from 5 independent experiments. The last column displays the average value of each peak for which the overlap of the Gaussian distributions are integrated.

| | Average |
|---|---|
| G(pA) | 16.2 ± 0.5 |
| T(pA) | 17.6 ± 0.6 |
| A(pA) | 18.6 ± 0.6 |
| C(pA) | 20.2 ± 0.5 |

In experiments where all 4 nucleotides are present, the Gaussians from all 4 nucleotides have an overlap. The statistics were calculated for the binding signal from one nucleotide to be identified as itself or another nucleotide from the level of overlap between the Gaussian distribution of this nucleotide and that of its neighbors.

Figure 6:
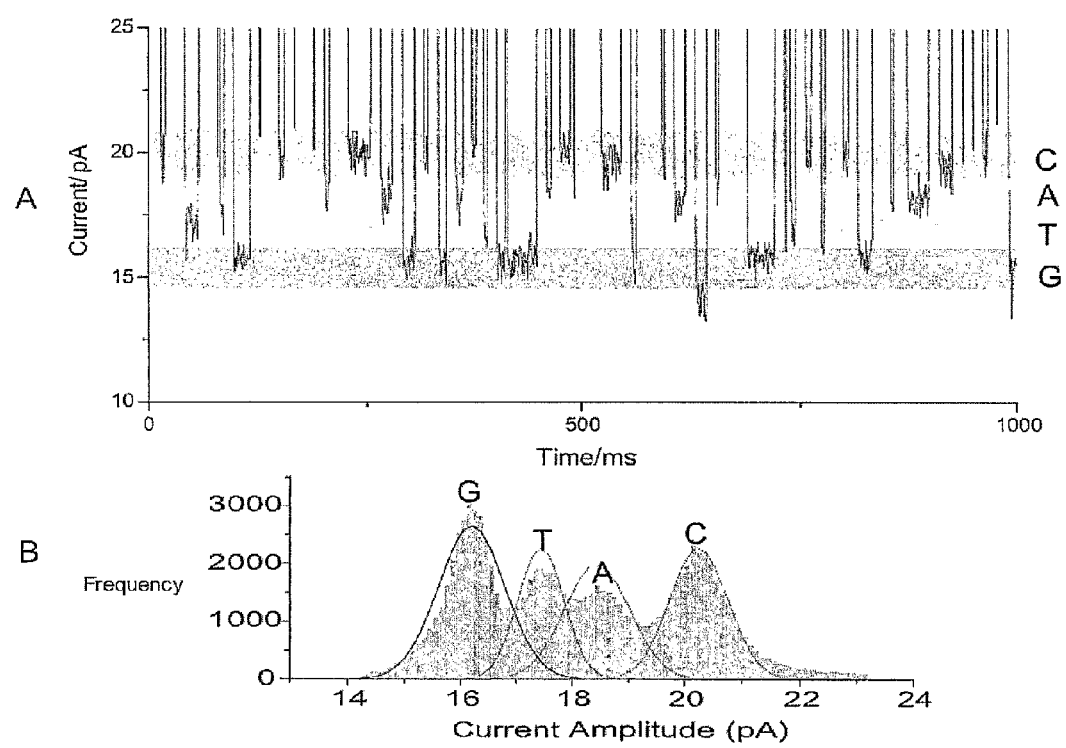
FIG. 6 shows simultaneous detection of dXMP. A shows the current trace of a single (M113R)$_7$ mutant inserted in a phospholipid bilayer, +130 mV potential is applied between the Ag/AgCl electrodes. The buffer is Tris-HCl 25 mM pH 8.0 with 1M KCl. 40 µM am$_7$-βCD is present in the trans chamber. 5 µM of dGMP, dTMP, dAMP, and dCMP are added to the cis chamber. The colored bands illustrate the amplitude distribution of each dXMP. B displays an all point histogram from a current trace of 8000 binding events. Each peak is superimposed with the statistical distribution of each dXMP.
Figure 7:
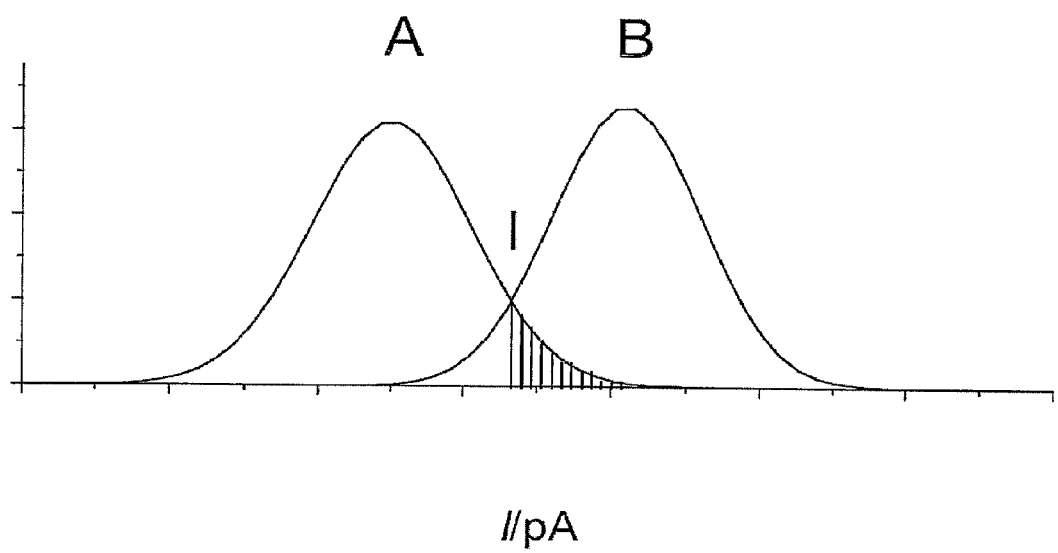
FIG. 7 shows the statistical method. Two Gaussian distributions A and B overlap at the point of intersection I. The area of Gaussian A beyond the point of intersection I is integrated and represents the probability of population A to be identified as population B.

The point of intersection between the two Gaussians is calculated form the respective peak positions (given by the experiment with mixed nucleotides), and σ values for each distribution (given by the fitting of individual nucleotide experiments). The accuracy probability is given by integrating the area of the Gaussian that is beyond the intercept value with the neighboring Gaussian (FIG. 6, Table 4). The first column of Table 4 is the nucleotide that interacts with the nanopore, and the first row is what is read from the corresponding current amplitude.

TABLE 4

Shows the probability of the added nucleotide (vertical) to be detected as itself or another nucleotide (horizontal).

| | $G_{read}$ | $T_{read}$ | $A_{read}$ | $C_{read}$ |
|---|---|---|---|---|
| $G_{added}$ | 0.88 | 0.12 | 0 | 0 |
| $T_{added}$ | 0.06 | 0.83 | 0.11 | 0 |
| $A_{added}$ | 0 | 0.19 | 0.74 | 0.07 |
| $C_{added}$ | 0 | 0 | 0.06 | 0.94 |

3. Conclusion

The results presented indicate that stochastic sensing is a promising alternative for the identification of single nucleotides. It also means that exonuclease sequencing can be used as a cheap, rapid, and simple DNA sequencing method at the single molecule level. Exonucleas sequencing is also a cheap method of sequencing DNA because it does not require expensive reagents, such as fluorophores.

All points histograms are a sufficient analysis method to identify each nucleotide with an accuracy ranging from 74 to 94% (Table 4). The dwell time values of the XMP and dXMP are too similar in the conditions to further differenciate each analyte. The statistics drawn from the amplitude histograms can be further improved by compensating for the cyclodextrin current levels as shown in FIG. 4. The current amplitude difference between each dXMP is about 1 pA. This resolution depends on a number of parameters as follows.

Voltage Dependence

The binding events are voltage dependent. At 50 mV, very few binding events are observed, suggesting that a minimum field is required to drive the dXMP and XMP to the binding site. At +150 and +200 mV the amplitudes no longer allow to differentiate the nucleotides. +130 mV proved to be the best voltage for deoxyribo nucleotides 5' monophosphate, and +110 mV yielded the best resolution for ribo nucleotides 5' monophosphate.

Salt Concentration

Tris-HCl pH 8 buffer 0.5, 1, and 2M KCl were tested. From the all points amplitude histograms, the best resolution between the peaks was obtained at 1M KCl.

pH Dependence

The current amplitudes are pH dependent, Tris-HCl buffer 1M KCl at pH 7.5, 8.0, 8.2, 8.5, 9.0, and 9.5 were tested. At pH 8.0 and above two current levels are observed upon binding of $am_7$-βCD (FIG. 4). At pH 7.5 the heptakis 6 amino β-cyclodextrin displays a third current level (not shown). It causes dTMP to display two types of events with different amplitudes, one of which is within the range of dGMP events, thus leading to a loss of resolution. At pH 9.5, the nucleotide binding events are no longer observed. The best peak separation is obtained at pH 8.0.

Salt Dependence

The resolution between dXMPs and XMPs is better with KCl than with NaCl or CsCl. 1M KCl yields better resolution than 2M KCl. The use of KBr did not allow the identification of the different nucleotides as each binding event led to a complete block of the transient complex $(M113R)_7$/$am_7$-βCD.

Temperature Dependence

Lowering the temperature to 14° C. or increasing it to 50° C. did not interfere with the detection of the dXMP/XMP. However, it did not improve the resolution of the amplitude histograms.

Other α-Hemolysin Mutants $(M113N)_7$ was seen to bind $am_7$-βCD but no nucleotide detection was observed. $(M113F)_7$ and $(M113F/147K)_7$ didn't yield detection whether $am_7$-βCD was added or not. $(M113K)_7$ was tested in the same conditions. In this case, the recording is very similar to that of FIG. 1. The nucleotide binding was detected with $(M113K)_7$ mutant and $am_7$-βCD but the peak separation between the nucleotides was smaller than when $(M113R)_7$ was used.

Ribonucleotides 5' Monophosphate

XMP were successfully identified with this method, the resolution between each base was inferior to that of dXMP with peak separations smaller than 1 pA for U, A, and C. The all point histogram current amplitudes appear in the same order as those of dXMPs, with GMP displaying the lowest current (largest blocking), followed by UMP, AMP, and CMP with the highest current amplitude (smallest blocking). The optimal voltage for XMP identification was found to be +110 mV at pH 8.0 1M KCl.

Mechanism

The $(M113R)_7$/$am_7$-βCD transient complex has also shown to bind and differentiate glucose phosphates (glucose 1P and galactose 1P). It suggests a strong interaction between the arginine ring on one side, the phosphate group and the amine ring from the $am_7$-βCD on the other side. Unmodified β-cyclodextrin does not yield any detection. Little difference is observed between XMP and dXMP suggesting that the hydroxyl groups do not play a large role in the binding.

The invention claimed is:

1. A method of distinguishing an individual monophosphate nucleotide, comprising:
   (a) contacting the monophosphate nucleotide with a transmembrane protein pore so that the monophosphate nucleotide interacts with the pore, wherein the pore comprises a molecular adaptor that facilitates the interaction between the monophosphate nucleotide and the pore, wherein the molecular adaptor is a cyclodextrin; and
   (b) measuring a current passing through the pore during the interaction and thereby distinguishing the monophosphate nucleotide from other monophosphate nucleotides.

2. A method according to claim 1, wherein the interaction involves the monophosphate nucleotide reversibly binding to the channel of the pore.

3. A method according to claim 1, wherein the pore is α-hemolysin as shown in SEQ ID NO: 2 or a variant thereof.

4. A method according to claim 3, wherein the variant is $(M113R)_7$.

5. A method according to claim 1, wherein the molecular adaptor is a heptakis-6-amino-β-cyclodextrin ($am_7$-β-CD).

6. A method according to claim 1, wherein the individual monophosphate nucleotide is a monophosphate ribonucleotide.

7. A method according to claim 6, further comprising before step (a) digesting a ribonucleic acid (RNA) sequence to provide the individual monophosphate nucleotide.

8. A method according to claim 1, wherein the individual monophosphate nucleotide is a monophosphate deoxyribonucleotide.

9. A method according to claim 8, further comprising before step (a) digesting a deoxyribonucleic acid (DNA) sequence to provide the individual monophosphate nucleotide.

10. A method according to claim 7, wherein more than one of the individual monophosphate nucleotides of the RNA sequence are contacted with the pore in a sequential manner such that the identity of the whole or part of the sequence may be determined.

11. A method of sequencing a target nucleic acid sequence, comprising:
    (a) digesting an individual monophosphate nucleotide from one end of the target sequence using a processive exonuclease;
    (b) contacting the monophosphate nucleotide with a transmembrane protein pore so that the monophosphate nucleotide interacts with the pore, wherein the pore comprises a molecular adaptor that facilitates the interaction between the monophosphate nucleotide and the pore, wherein the molecular adaptor is a cyclodextrin;
    (c) measuring a current passing through the pore during the interaction and thereby determining the identity of the individual monophosphate nucleotide; and
    (d) repeating steps (a) to (c) at the same end of the target sequence and thereby determining the sequence of the nucleic acid.

12. A method according to claim 9, wherein more than one of the individual monophosphate nucleotides of the DNA sequence are contacted with the pore in a sequential manner such that the identity of the whole or part of the sequence may be determined.

* * * * *

UNITED STATES PATENT AND TRADEMARK OFFICE
CERTIFICATE OF CORRECTION

| | | |
|---|---|---|
| PATENT NO. | : 8,785,211 B2 | Page 1 of 1 |
| APPLICATION NO. | : 13/338794 | |
| DATED | : July 22, 2014 | |
| INVENTOR(S) | : Hagan Bayley et al. | |

It is certified that error appears in the above-identified patent and that said Letters Patent is hereby corrected as shown below:

On the Title Page, Item (63), the Related U.S. Application Data section should read:

--Continuation of U.S. Serial Number 12/093,610, filed on July 28, 2008 (now Pat. No. 8,105,846), which is a 35 U.S.C. § 371 national stage filing of PCT Application No. PCT/GB2006/004265, filed on November 15, 2006.--

Signed and Sealed this
Third Day of February, 2015

Michelle K. Lee
*Deputy Director of the United States Patent and Trademark Office*

SEQUENCE LISTING

```
<160> NUMBER OF SEQ ID NOS: 9

<210> SEQ ID NO 1
<211> LENGTH: 882
<212> TYPE: DNA
<213> ORGANISM: Staphylococcus aureus
<220> FEATURE:
<221> NAME/KEY: CDS
<222> LOCATION: (1)..(879)

<400> SEQUENCE: 1 gca gat tct gat att aat att aaa acc ggt act aca gat att gga agc        48
Ala Asp Ser Asp Ile Asn Ile Lys Thr Gly Thr Thr Asp Ile Gly Ser
1               5                   10                  15 aat act aca gta aaa aca ggt gat tta gtc act tat gat aaa gaa aat        96
Asn Thr Thr Val Lys Thr Gly Asp Leu Val Thr Tyr Asp Lys Glu Asn
                20                  25                  30 ggc atg cac aaa aaa gta ttt tat agt ttt atc gat gat aaa aat cac       144
Gly Met His Lys Lys Val Phe Tyr Ser Phe Ile Asp Asp Lys Asn His
            35                  40                  45 aat aaa aaa ctg cta gtt att aga acg aaa ggt acc att gct ggt caa       192
Asn Lys Lys Leu Leu Val Ile Arg Thr Lys Gly Thr Ile Ala Gly Gln
        50                  55                  60 tat aga gtt tat agc gaa gaa ggt gct aac aaa agt ggt tta gcc tgg       240
Tyr Arg Val Tyr Ser Glu Glu Gly Ala Asn Lys Ser Gly Leu Ala Trp
65                  70                  75                  80 cct tca gcc ttt aag gta cag ttg caa cta cct gat aat gaa gta gct       288
Pro Ser Ala Phe Lys Val Gln Leu Gln Leu Pro Asp Asn Glu Val Ala
                85                  90                  95 caa ata tct gat tac tat cca aga aat tcg att gat aca aaa gag tat       336
Gln Ile Ser Asp Tyr Tyr Pro Arg Asn Ser Ile Asp Thr Lys Glu Tyr
                100                 105                 110
```

```
atg agt act tta act tat gga ttc aac ggt aat gtt act ggt gat gat    384
Met Ser Thr Leu Thr Tyr Gly Phe Asn Gly Asn Val Thr Gly Asp Asp
    115                 120                 125 aca gga aaa att ggc ggc ctt att ggt gca aat gtt tcg att ggt cat    432
Thr Gly Lys Ile Gly Gly Leu Ile Gly Ala Asn Val Ser Ile Gly His
130                 135                 140 aca ctg aaa tat gtt caa cct gat ttc aaa aca att tta gag agc cca    480
Thr Leu Lys Tyr Val Gln Pro Asp Phe Lys Thr Ile Leu Glu Ser Pro
145                 150                 155                 160 act gat aaa aaa gta ggc tgg aaa gtg ata ttt aac aat atg gtg aat    528
Thr Asp Lys Lys Val Gly Trp Lys Val Ile Phe Asn Asn Met Val Asn
                165                 170                 175 caa aat tgg gga cca tat gat aga gat tct tgg aac ccg gta tat ggc    576
Gln Asn Trp Gly Pro Tyr Asp Arg Asp Ser Trp Asn Pro Val Tyr Gly
            180                 185                 190 aat caa ctt ttc atg aaa act aga aat ggt tct atg aaa gca gca gat    624
Asn Gln Leu Phe Met Lys Thr Arg Asn Gly Ser Met Lys Ala Ala Asp
        195                 200                 205 aac ttc ctt gat cct aac aaa gca agt tct cta tta tct tca ggg ttt    672
Asn Phe Leu Asp Pro Asn Lys Ala Ser Ser Leu Leu Ser Ser Gly Phe
210                 215                 220 tca cca gac ttc gct aca gtt att act atg gat aga aaa gca tcc aaa    720
Ser Pro Asp Phe Ala Thr Val Ile Thr Met Asp Arg Lys Ala Ser Lys
225                 230                 235                 240 caa caa aca aat ata gat gta ata tac gaa cga gtt cgt gat gat tac    768
Gln Gln Thr Asn Ile Asp Val Ile Tyr Glu Arg Val Arg Asp Asp Tyr
                245                 250                 255 caa ttg cat tgg act tca aca aat tgg aaa ggt acc aat act aaa gat    816
Gln Leu His Trp Thr Ser Thr Asn Trp Lys Gly Thr Asn Thr Lys Asp
            260                 265                 270 aaa tgg aca gat cgt tct tca gaa aga tat aaa atc gat tgg gaa aaa    864
Lys Trp Thr Asp Arg Ser Ser Glu Arg Tyr Lys Ile Asp Trp Glu Lys
        275                 280                 285 gaa gaa atg aca aat taa                                            882
Glu Glu Met Thr Asn
    290

<210> SEQ ID NO 2
<211> LENGTH: 293
<212> TYPE: PRT
<213> ORGANISM: Staphylococcus aureus

<400> SEQUENCE: 2

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125
```

```
Thr Gly Lys Ile Gly Gly Leu Ile Gly Ala Asn Val Ser Ile Gly His
        130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 3
<211> LENGTH: 1300
<212> TYPE: DNA
<213> ORGANISM: Artificial sequence
<220> FEATURE:
<223> OTHER INFORMATION: M113H alpha hemolysin mutant
<220> FEATURE:
<221> NAME/KEY: CDS
<222> LOCATION: (39)..(920)
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (926)..(926)
<223> OTHER INFORMATION: n is a, c, g, or t
<220> FEATURE:
<221> NAME/KEY: misc_feature
<222> LOCATION: (991)..(991)
<223> OTHER INFORMATION: n is a, c, g, or t
<220> FEATURE:
<221> NAME/KEY: misc_feature
<222> LOCATION: (994)..(994)
<223> OTHER INFORMATION: n is a, c, g, or t
<220> FEATURE:
<221> NAME/KEY: misc_feature
<222> LOCATION: (998)..(998)
<223> OTHER INFORMATION: n is a, c, g, or t
<220> FEATURE:
<221> NAME/KEY: misc_feature
<222> LOCATION: (1001)..(1001)
<223> OTHER INFORMATION: n is a, c, g, or t
<220> FEATURE:
<221> NAME/KEY: misc_feature
<222> LOCATION: (1003)..(1003)
```

```
<223> OTHER INFORMATION: n is a, c, g, or t
<220> FEATURE:
<221> NAME/KEY: misc_feature
<222> LOCATION: (1010)..(1010)
<223> OTHER INFORMATION: n is a, c, g, or t
<220> FEATURE:
<221> NAME/KEY: misc_feature
<222> LOCATION: (1014)..(1014)
<223> OTHER INFORMATION: n is a, c, g, or t
<220> FEATURE:
<221> NAME/KEY: misc_feature
<222> LOCATION: (1031)..(1031)
<223> OTHER INFORMATION: n is a, c, g, or t
<220> FEATURE:
<221> NAME/KEY: misc_feature
<222> LOCATION: (1041)..(1041)
<223> OTHER INFORMATION: n is a, c, g, or t
<220> FEATURE:
<221> NAME/KEY: misc_feature
<222> LOCATION: (1052)..(1052)
<223> OTHER INFORMATION: n is a, c, g, or t
<220> FEATURE:
<221> NAME/KEY: misc_feature
<222> LOCATION: (1067)..(1067)
<223> OTHER INFORMATION: n is a, c, g, or t
<220> FEATURE:
<221> NAME/KEY: misc_feature
<222> LOCATION: (1083)..(1083)
<223> OTHER INFORMATION: n is a, c, g, or t
<220> FEATURE:
<221> NAME/KEY: misc_feature
<222> LOCATION: (1085)..(1085)
<223> OTHER INFORMATION: n is a, c, g, or t
<220> FEATURE:
<221> NAME/KEY: misc_feature
<222> LOCATION: (1087)..(1087)
<223> OTHER INFORMATION: n is a, c, g, or t
<220> FEATURE:
<221> NAME/KEY: misc_feature
<222> LOCATION: (1097)..(1098)
<223> OTHER INFORMATION: n is a, c, g, or t
<220> FEATURE:
<221> NAME/KEY: misc_feature
<222> LOCATION: (1100)..(1100)
<223> OTHER INFORMATION: n is a, c, g, or t
<220> FEATURE:
<221> NAME/KEY: misc_feature
<222> LOCATION: (1103)..(1104)
<223> OTHER INFORMATION: n is a, c, g, or t
<220> FEATURE:
<221> NAME/KEY: misc_feature
<222> LOCATION: (1110)..(1110)
<223> OTHER INFORMATION: n is a, c, g, or t
<220> FEATURE:
<221> NAME/KEY: misc_feature
<222> LOCATION: (1117)..(1117)
<223> OTHER INFORMATION: n is a, c, g, or t
<220> FEATURE:
<221> NAME/KEY: misc_feature
<222> LOCATION: (1128)..(1128)
<223> OTHER INFORMATION: n is a, c, g, or t
<220> FEATURE:
<221> NAME/KEY: misc_feature
<222> LOCATION: (1131)..(1131)
<223> OTHER INFORMATION: n is a, c, g, or t
<220> FEATURE:
<221> NAME/KEY: misc_feature
<222> LOCATION: (1136)..(1136)
<223> OTHER INFORMATION: n is a, c, g, or t
<220> FEATURE:
<221> NAME/KEY: misc_feature
<222> LOCATION: (1140)..(1140)
<223> OTHER INFORMATION: n is a, c, g, or t
<220> FEATURE:
<221> NAME/KEY: misc_feature
<222> LOCATION: (1143)..(1143)
<223> OTHER INFORMATION: n is a, c, g, or t
<220> FEATURE:
<221> NAME/KEY: misc_feature
```

```
<222> LOCATION: (1145)..(1145)
<223> OTHER INFORMATION: n is a, c, g, or t
<220> FEATURE:
<221> NAME/KEY: misc_feature
<222> LOCATION: (1148)..(1148)
<223> OTHER INFORMATION: n is a, c, g, or t
<220> FEATURE:
<221> NAME/KEY: misc_feature
<222> LOCATION: (1151)..(1151)
<223> OTHER INFORMATION: n is a, c, g, or t
<220> FEATURE:
<221> NAME/KEY: misc_feature
<222> LOCATION: (1155)..(1155)
<223> OTHER INFORMATION: n is a, c, g, or t
<220> FEATURE:
<221> NAME/KEY: misc_feature
<222> LOCATION: (1160)..(1160)
<223> OTHER INFORMATION: n is a, c, g, or t
<220> FEATURE:
<221> NAME/KEY: misc_feature
<222> LOCATION: (1164)..(1165)
<223> OTHER INFORMATION: n is a, c, g, or t
<220> FEATURE:
<221> NAME/KEY: misc_feature
<222> LOCATION: (1167)..(1167)
<223> OTHER INFORMATION: n is a, c, g, or t
<220> FEATURE:
<221> NAME/KEY: misc_feature
<222> LOCATION: (1169)..(1169)
<223> OTHER INFORMATION: n is a, c, g, or t
<220> FEATURE:
<221> NAME/KEY: misc_feature
<222> LOCATION: (1171)..(1171)
<223> OTHER INFORMATION: n is a, c, g, or t
<220> FEATURE:
<221> NAME/KEY: misc_feature
<222> LOCATION: (1175)..(1176)
<223> OTHER INFORMATION: n is a, c, g, or t
<220> FEATURE:
<221> NAME/KEY: misc_feature
<222> LOCATION: (1180)..(1180)
<223> OTHER INFORMATION: n is a, c, g, or t
<220> FEATURE:
<221> NAME/KEY: misc_feature
<222> LOCATION: (1182)..(1184)
<223> OTHER INFORMATION: n is a, c, g, or t
<220> FEATURE:
<221> NAME/KEY: misc_feature
<222> LOCATION: (1188)..(1188)
<223> OTHER INFORMATION: n is a, c, g, or t
<220> FEATURE:
<221> NAME/KEY: misc_feature
<222> LOCATION: (1191)..(1191)
<223> OTHER INFORMATION: n is a, c, g, or t
<220> FEATURE:
<221> NAME/KEY: misc_feature
<222> LOCATION: (1193)..(1193)
<223> OTHER INFORMATION: n is a, c, g, or t
<220> FEATURE:
<221> NAME/KEY: misc_feature
<222> LOCATION: (1196)..(1196)
<223> OTHER INFORMATION: n is a, c, g, or t
<220> FEATURE:
<221> NAME/KEY: misc_feature
<222> LOCATION: (1201)..(1201)
<223> OTHER INFORMATION: n is a, c, g, or t
<220> FEATURE:
<221> NAME/KEY: misc_feature
<222> LOCATION: (1206)..(1206)
<223> OTHER INFORMATION: n is a, c, g, or t
<220> FEATURE:
<221> NAME/KEY: misc_feature
<222> LOCATION: (1208)..(1208)
<223> OTHER INFORMATION: n is a, c, g, or t
<220> FEATURE:
<221> NAME/KEY: misc_feature
<222> LOCATION: (1210)..(1210)
<223> OTHER INFORMATION: n is a, c, g, or t
<220> FEATURE:
```

```
<221> NAME/KEY: misc_feature
<222> LOCATION: (1214)..(1214)
<223> OTHER INFORMATION: n is a, c, g, or t
<220> FEATURE:
<221> NAME/KEY: misc_feature
<222> LOCATION: (1217)..(1221)
<223> OTHER INFORMATION: n is a, c, g, or t
<220> FEATURE:
<221> NAME/KEY: misc_feature
<222> LOCATION: (1223)..(1223)
<223> OTHER INFORMATION: n is a, c, g, or t
<220> FEATURE:
<221> NAME/KEY: misc_feature
<222> LOCATION: (1229)..(1229)
<223> OTHER INFORMATION: n is a, c, g, or t
<220> FEATURE:
<221> NAME/KEY: misc_feature
<222> LOCATION: (1231)..(1231)
<223> OTHER INFORMATION: n is a, c, g, or t
<220> FEATURE:
<221> NAME/KEY: misc_feature
<222> LOCATION: (1238)..(1238)
<223> OTHER INFORMATION: n is a, c, g, or t
<220> FEATURE:
<221> NAME/KEY: misc_feature
<222> LOCATION: (1241)..(1243)
<223> OTHER INFORMATION: n is a, c, g, or t
<220> FEATURE:
<221> NAME/KEY: misc_feature
<222> LOCATION: (1255)..(1256)
<223> OTHER INFORMATION: n is a, c, g, or t
<220> FEATURE:
<221> NAME/KEY: misc_feature
<222> LOCATION: (1258)..(1260)
<223> OTHER INFORMATION: n is a, c, g, or t
<220> FEATURE:
<221> NAME/KEY: misc_feature
<222> LOCATION: (1262)..(1264)
<223> OTHER INFORMATION: n is a, c, g, or t
<220> FEATURE:
<221> NAME/KEY: misc_feature
<222> LOCATION: (1267)..(1267)
<223> OTHER INFORMATION: n is a, c, g, or t
<220> FEATURE:
<221> NAME/KEY: misc_feature
<222> LOCATION: (1270)..(1270)
<223> OTHER INFORMATION: n is a, c, g, or t
<220> FEATURE:
<221> NAME/KEY: misc_feature
<222> LOCATION: (1273)..(1273)
<223> OTHER INFORMATION: n is a, c, g, or t
<220> FEATURE:
<221> NAME/KEY: misc_feature
<222> LOCATION: (1282)..(1283)
<223> OTHER INFORMATION: n is a, c, g, or t
<220> FEATURE:
<221> NAME/KEY: misc_feature
<222> LOCATION: (1288)..(1288)
<223> OTHER INFORMATION: n is a, c, g, or t
<220> FEATURE:
<221> NAME/KEY: misc_feature
<222> LOCATION: (1291)..(1293)
<223> OTHER INFORMATION: n is a, c, g, or t
<220> FEATURE:
<221> NAME/KEY: misc_feature
<222> LOCATION: (1295)..(1295)
<223> OTHER INFORMATION: n is a, c, g, or t
<220> FEATURE:
<221> NAME/KEY: misc_feature
<222> LOCATION: (1300)..(1300)
<223> OTHER INFORMATION: n is a, c, g, or t

<400> SEQUENCE: 3
gttctgttta actttaagaa gggagatata catatgag cag att ctg ata ttn acn      56
                                         Gln Ile Leu Ile Xaa Thr
                                         1               5 tnn gcg acc ggt act aca gat att gga agc aat act aca gta aaa aca      104
```

```
Xaa Ala Thr Gly Thr Thr Asp Ile Gly Ser Asn Thr Thr Val Lys Thr
             10                  15                  20 ggt gat tta gtc act tat gat aaa gaa aat ggc atg cac aaa aaa gta      152
Gly Asp Leu Val Thr Tyr Asp Lys Glu Asn Gly Met His Lys Lys Val
         25                  30                  35 ttt tat agt ttt atc gat gat aaa aat cac aat aaa aaa ctg cta gtt      200
Phe Tyr Ser Phe Ile Asp Asp Lys Asn His Asn Lys Lys Leu Leu Val
     40                  45                  50 att aga aca aaa ggt acc att gct ggt caa tat aga gtt tat agc gaa      248
Ile Arg Thr Lys Gly Thr Ile Ala Gly Gln Tyr Arg Val Tyr Ser Glu
55                  60                  65                  70 gaa ggt gct aac aaa agt ggt tta gcc tgg cct tca gcc ttt aag gta      296
Glu Gly Ala Asn Lys Ser Gly Leu Ala Trp Pro Ser Ala Phe Lys Val
                 75                  80                  85 cag ttg caa cta cct gat aat gaa gta gct caa ata tct gat tac tat      344
Gln Leu Gln Leu Pro Asp Asn Glu Val Ala Gln Ile Ser Asp Tyr Tyr
             90                  95                 100 ccg cgg aat tcg att gat aca aaa gag tat cac agt acg tta acg tac      392
Pro Arg Asn Ser Ile Asp Thr Lys Glu Tyr His Ser Thr Leu Thr Tyr
        105                 110                 115 gga ttc aac ggt aac ctt act ggt gat gat act agt aaa att gga ggc      440
Gly Phe Asn Gly Asn Leu Thr Gly Asp Asp Thr Ser Lys Ile Gly Gly
    120                 125                 130 ctt att ggg gcc cag gtt tcc cta ggt cat aca ctt aag tat gtt caa      488
Leu Ile Gly Ala Gln Val Ser Leu Gly His Thr Leu Lys Tyr Val Gln
135                 140                 145                 150 cct gat ttc aaa aca att ctc gag agc cca act gat aaa aaa gta ggc      536
Pro Asp Phe Lys Thr Ile Leu Glu Ser Pro Thr Asp Lys Lys Val Gly
                155                 160                 165 tgg aaa gtg ata ttt aac aat atg gtg aat caa aat tgg gga cca tac      584
Trp Lys Val Ile Phe Asn Asn Met Val Asn Gln Asn Trp Gly Pro Tyr
            170                 175                 180 gat cga gat tct tgg aac ccg gta tat ggc aat caa ctt ttc atg aag      632
Asp Arg Asp Ser Trp Asn Pro Val Tyr Gly Asn Gln Leu Phe Met Lys
        185                 190                 195 act aga aat ggt tct atg aaa gca gca gat aac ttc ctt gat cct aac      680
Thr Arg Asn Gly Ser Met Lys Ala Ala Asp Asn Phe Leu Asp Pro Asn
    200                 205                 210 aaa gca agt tcc cta tta tct tca ggg ttt tca cca gac ttc gct aca      728
Lys Ala Ser Ser Leu Leu Ser Ser Gly Phe Ser Pro Asp Phe Ala Thr
215                 220                 225                 230 gtt att act atg gat aga aaa gca tcc aaa caa caa aca aat ata gat      776
Val Ile Thr Met Asp Arg Lys Ala Ser Lys Gln Gln Thr Asn Ile Asp
                235                 240                 245 gta ata tac gaa cga gtt cgt gat gat tac caa ttg cat tgg act tca      824
Val Ile Tyr Glu Arg Val Arg Asp Asp Tyr Gln Leu His Trp Thr Ser
            250                 255                 260 cca aat tgg aaa ggt acc aat act aaa gat aaa tgg aca gat cgt tct      872
Pro Asn Trp Lys Gly Thr Asn Thr Lys Asp Lys Trp Thr Asp Arg Ser
        265                 270                 275 tca gaa aga tat aaa atc gat tgg gaa aaa gaa gaa atg aca aat taa      920
Ser Glu Arg Tyr Lys Ile Asp Trp Glu Lys Glu Glu Met Thr Asn
    280                 285                 290 tgtaanttat ttgtacatgt acaaataaat ataatttata actttagccg aagctggatc    980
cggctgctac naanccccnaa ngnagctgan ttgnctgctg cccccctgac natactagca  1040
naccccttgg gncectaacg ggtctgnggg gtttttgctg aangngnact tttccgnnan   1100 tcnnecccggn cccccenggt gaaatccnaa ncccenaacn gggngntgnta ncaantttan 1160
```

-continued

```
tggnncntna ntttnnaaan cnnntaantt ngnaanccccc nttttncnan ggcnaannnn   1220 nanccttna naaaaaancc nnngggggggg tttcnntnnn annnccnttn aangggcccc    1280 cnngggnaa nnntnggggn                                                 1300
```

<210> SEQ ID NO 4
<211> LENGTH: 293
<212> TYPE: PRT
<213> ORGANISM: Artificial sequence
<220> FEATURE:
<221> NAME/KEY: misc_feature
<222> LOCATION: (5)..(5)
<223> OTHER INFORMATION: The 'Xaa' at location 5 stands for Leu, or Phe.
<220> FEATURE:
<221> NAME/KEY: misc_feature
<222> LOCATION: (7)..(7)
<223> OTHER INFORMATION: The 'Xaa' at location 7 stands for Tyr, Trp,
      Cys, Ser, Leu, or Phe.
<220> FEATURE:
<223> OTHER INFORMATION: M113H alpha hemolysin mutant

<400> SEQUENCE: 4

Gln Ile Leu Ile Xaa Thr Xaa Ala Thr Gly Thr Thr Asp Ile Gly Ser
 1               5                  10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
 65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

His Ser Thr Leu Thr Tyr Gly Phe Asn Gly Asn Leu Thr Gly Asp Asp
        115                 120                 125

Thr Ser Lys Ile Gly Gly Leu Ile Gly Ala Gln Val Ser Leu Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Pro Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 5
<211> LENGTH: 1300
<212> TYPE: DNA
<213> ORGANISM: Artificial sequence
<220> FEATURE:
<223> OTHER INFORMATION: M113K alpha hemolysin mutant
<220> FEATURE:
<221> NAME/KEY: CDS
<222> LOCATION: (39)..(920)
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (926)..(926)
<223> OTHER INFORMATION: n is a, c, g, or t
<220> FEATURE:
<221> NAME/KEY: misc_feature
<222> LOCATION: (991)..(991)
<223> OTHER INFORMATION: n is a, c, g, or t
<220> FEATURE:
<221> NAME/KEY: misc_feature
<222> LOCATION: (994)..(994)
<223> OTHER INFORMATION: n is a, c, g, or t
<220> FEATURE:
<221> NAME/KEY: misc_feature
<222> LOCATION: (998)..(998)
<223> OTHER INFORMATION: n is a, c, g, or t
<220> FEATURE:
<221> NAME/KEY: misc_feature
<222> LOCATION: (1001)..(1001)
<223> OTHER INFORMATION: n is a, c, g, or t
<220> FEATURE:
<221> NAME/KEY: misc_feature
<222> LOCATION: (1003)..(1003)
<223> OTHER INFORMATION: n is a, c, g, or t
<220> FEATURE:
<221> NAME/KEY: misc_feature
<222> LOCATION: (1010)..(1010)
<223> OTHER INFORMATION: n is a, c, g, or t
<220> FEATURE:
<221> NAME/KEY: misc_feature
<222> LOCATION: (1014)..(1014)
<223> OTHER INFORMATION: n is a, c, g, or t
<220> FEATURE:
<221> NAME/KEY: misc_feature
<222> LOCATION: (1031)..(1031)
<223> OTHER INFORMATION: n is a, c, g, or t
<220> FEATURE:
<221> NAME/KEY: misc_feature
<222> LOCATION: (1041)..(1041)
<223> OTHER INFORMATION: n is a, c, g, or t
<220> FEATURE:
<221> NAME/KEY: misc_feature
<222> LOCATION: (1052)..(1052)
<223> OTHER INFORMATION: n is a, c, g, or t
<220> FEATURE:
<221> NAME/KEY: misc_feature
<222> LOCATION: (1067)..(1067)
<223> OTHER INFORMATION: n is a, c, g, or t
<220> FEATURE:
<221> NAME/KEY: misc_feature
<222> LOCATION: (1083)..(1083)
<223> OTHER INFORMATION: n is a, c, g, or t
<220> FEATURE:
<221> NAME/KEY: misc_feature -continued

```
<222> LOCATION: (1085)..(1085)
<223> OTHER INFORMATION: n is a, c, g, or t
<220> FEATURE:
<221> NAME/KEY: misc_feature
<222> LOCATION: (1087)..(1087)
<223> OTHER INFORMATION: n is a, c, g, or t
<220> FEATURE:
<221> NAME/KEY: misc_feature
<222> LOCATION: (1097)..(1098)
<223> OTHER INFORMATION: n is a, c, g, or t
<220> FEATURE:
<221> NAME/KEY: misc_feature
<222> LOCATION: (1100)..(1100)
<223> OTHER INFORMATION: n is a, c, g, or t
<220> FEATURE:
<221> NAME/KEY: misc_feature
<222> LOCATION: (1103)..(1104)
<223> OTHER INFORMATION: n is a, c, g, or t
<220> FEATURE:
<221> NAME/KEY: misc_feature
<222> LOCATION: (1110)..(1110)
<223> OTHER INFORMATION: n is a, c, g, or t
<220> FEATURE:
<221> NAME/KEY: misc_feature
<222> LOCATION: (1117)..(1117)
<223> OTHER INFORMATION: n is a, c, g, or t
<220> FEATURE:
<221> NAME/KEY: misc_feature
<222> LOCATION: (1128)..(1128)
<223> OTHER INFORMATION: n is a, c, g, or t
<220> FEATURE:
<221> NAME/KEY: misc_feature
<222> LOCATION: (1131)..(1131)
<223> OTHER INFORMATION: n is a, c, g, or t
<220> FEATURE:
<221> NAME/KEY: misc_feature
<222> LOCATION: (1136)..(1136)
<223> OTHER INFORMATION: n is a, c, g, or t
<220> FEATURE:
<221> NAME/KEY: misc_feature
<222> LOCATION: (1140)..(1140)
<223> OTHER INFORMATION: n is a, c, g, or t
<220> FEATURE:
<221> NAME/KEY: misc_feature
<222> LOCATION: (1143)..(1143)
<223> OTHER INFORMATION: n is a, c, g, or t
<220> FEATURE:
<221> NAME/KEY: misc_feature
<222> LOCATION: (1145)..(1145)
<223> OTHER INFORMATION: n is a, c, g, or t
<220> FEATURE:
<221> NAME/KEY: misc_feature
<222> LOCATION: (1148)..(1148)
<223> OTHER INFORMATION: n is a, c, g, or t
<220> FEATURE:
<221> NAME/KEY: misc_feature
<222> LOCATION: (1151)..(1151)
<223> OTHER INFORMATION: n is a, c, g, or t
<220> FEATURE:
<221> NAME/KEY: misc_feature
<222> LOCATION: (1155)..(1155)
<223> OTHER INFORMATION: n is a, c, g, or t
<220> FEATURE:
<221> NAME/KEY: misc_feature
<222> LOCATION: (1160)..(1160)
<223> OTHER INFORMATION: n is a, c, g, or t
<220> FEATURE:
<221> NAME/KEY: misc_feature
<222> LOCATION: (1164)..(1165)
<223> OTHER INFORMATION: n is a, c, g, or t
<220> FEATURE:
<221> NAME/KEY: misc_feature
<222> LOCATION: (1167)..(1167)
<223> OTHER INFORMATION: n is a, c, g, or t
<220> FEATURE:
<221> NAME/KEY: misc_feature
<222> LOCATION: (1169)..(1169)
<223> OTHER INFORMATION: n is a, c, g, or t
<220> FEATURE:
```

-continued

```
<221> NAME/KEY: misc_feature
<222> LOCATION: (1171)..(1171)
<223> OTHER INFORMATION: n is a, c, g, or t
<220> FEATURE:
<221> NAME/KEY: misc_feature
<222> LOCATION: (1175)..(1176)
<223> OTHER INFORMATION: n is a, c, g, or t
<220> FEATURE:
<221> NAME/KEY: misc_feature
<222> LOCATION: (1180)..(1180)
<223> OTHER INFORMATION: n is a, c, g, or t
<220> FEATURE:
<221> NAME/KEY: misc_feature
<222> LOCATION: (1182)..(1184)
<223> OTHER INFORMATION: n is a, c, g, or t
<220> FEATURE:
<221> NAME/KEY: misc_feature
<222> LOCATION: (1188)..(1188)
<223> OTHER INFORMATION: n is a, c, g, or t
<220> FEATURE:
<221> NAME/KEY: misc_feature
<222> LOCATION: (1191)..(1191)
<223> OTHER INFORMATION: n is a, c, g, or t
<220> FEATURE:
<221> NAME/KEY: misc_feature
<222> LOCATION: (1193)..(1193)
<223> OTHER INFORMATION: n is a, c, g, or t
<220> FEATURE:
<221> NAME/KEY: misc_feature
<222> LOCATION: (1196)..(1196)
<223> OTHER INFORMATION: n is a, c, g, or t
<220> FEATURE:
<221> NAME/KEY: misc_feature
<222> LOCATION: (1201)..(1201)
<223> OTHER INFORMATION: n is a, c, g, or t
<220> FEATURE:
<221> NAME/KEY: misc_feature
<222> LOCATION: (1206)..(1206)
<223> OTHER INFORMATION: n is a, c, g, or t
<220> FEATURE:
<221> NAME/KEY: misc_feature
<222> LOCATION: (1208)..(1208)
<223> OTHER INFORMATION: n is a, c, g, or t
<220> FEATURE:
<221> NAME/KEY: misc_feature
<222> LOCATION: (1210)..(1210)
<223> OTHER INFORMATION: n is a, c, g, or t
<220> FEATURE:
<221> NAME/KEY: misc_feature
<222> LOCATION: (1214)..(1214)
<223> OTHER INFORMATION: n is a, c, g, or t
<220> FEATURE:
<221> NAME/KEY: misc_feature
<222> LOCATION: (1217)..(1221)
<223> OTHER INFORMATION: n is a, c, g, or t
<220> FEATURE:
<221> NAME/KEY: misc_feature
<222> LOCATION: (1223)..(1223)
<223> OTHER INFORMATION: n is a, c, g, or t
<220> FEATURE:
<221> NAME/KEY: misc_feature
<222> LOCATION: (1229)..(1229)
<223> OTHER INFORMATION: n is a, c, g, or t
<220> FEATURE:
<221> NAME/KEY: misc_feature
<222> LOCATION: (1231)..(1231)
<223> OTHER INFORMATION: n is a, c, g, or t
<220> FEATURE:
<221> NAME/KEY: misc_feature
<222> LOCATION: (1238)..(1238)
<223> OTHER INFORMATION: n is a, c, g, or t
<220> FEATURE:
<221> NAME/KEY: misc_feature
<222> LOCATION: (1241)..(1243)
<223> OTHER INFORMATION: n is a, c, g, or t
<220> FEATURE:
<221> NAME/KEY: misc_feature
<222> LOCATION: (1255)..(1256)
<223> OTHER INFORMATION: n is a, c, g, or t
```

<220> FEATURE:
<221> NAME/KEY: misc_feature
<222> LOCATION: (1258)..(1260)
<223> OTHER INFORMATION: n is a, c, g, or t
<220> FEATURE:
<221> NAME/KEY: misc_feature
<222> LOCATION: (1262)..(1264)
<223> OTHER INFORMATION: n is a, c, g, or t
<220> FEATURE:
<221> NAME/KEY: misc_feature
<222> LOCATION: (1267)..(1267)
<223> OTHER INFORMATION: n is a, c, g, or t
<220> FEATURE:
<221> NAME/KEY: misc_feature
<222> LOCATION: (1270)..(1270)
<223> OTHER INFORMATION: n is a, c, g, or t
<220> FEATURE:
<221> NAME/KEY: misc_feature
<222> LOCATION: (1273)..(1273)
<223> OTHER INFORMATION: n is a, c, g, or t
<220> FEATURE:
<221> NAME/KEY: misc_feature
<222> LOCATION: (1282)..(1283)
<223> OTHER INFORMATION: n is a, c, g, or t
<220> FEATURE:
<221> NAME/KEY: misc_feature
<222> LOCATION: (1288)..(1288)
<223> OTHER INFORMATION: n is a, c, g, or t
<220> FEATURE:
<221> NAME/KEY: misc_feature
<222> LOCATION: (1291)..(1293)
<223> OTHER INFORMATION: n is a, c, g, or t
<220> FEATURE:
<221> NAME/KEY: misc_feature
<222> LOCATION: (1295)..(1295)
<223> OTHER INFORMATION: n is a, c, g, or t
<220> FEATURE:
<221> NAME/KEY: misc_feature
<222> LOCATION: (1300)..(1300)
<223> OTHER INFORMATION: n is a, c, g, or t

<400> SEQUENCE: 5

```
gttctgttta actttaagaa gggagatata catatgag cag att ctg ata ttn acn        56
                                   Gln Ile Leu Ile Xaa Thr
                                     1               5 tnn gcg acc ggt act aca gat att gga agc aat act aca gta aaa aca         104
Xaa Ala Thr Gly Thr Thr Asp Ile Gly Ser Asn Thr Thr Val Lys Thr
         10                  15                  20 ggt gat tta gtc act tat gat aaa gaa aat ggc atg cac aaa aaa gta        152
Gly Asp Leu Val Thr Tyr Asp Lys Glu Asn Gly Met His Lys Lys Val
 25                  30                  35 ttt tat agt ttt atc gat gat aaa aat cac aat aaa aaa ctg cta gtt        200
Phe Tyr Ser Phe Ile Asp Asp Lys Asn His Asn Lys Lys Leu Leu Val
     40                  45                  50 att aga aca aaa ggt acc att gct ggt caa tat aga gtt tat agc gaa        248
Ile Arg Thr Lys Gly Thr Ile Ala Gly Gln Tyr Arg Val Tyr Ser Glu
 55                  60                  65                  70 gaa ggt gct aac aaa agt ggt tta gcc tgg cct tca gcc ttt aag gta        296
Glu Gly Ala Asn Lys Ser Gly Leu Ala Trp Pro Ser Ala Phe Lys Val
                 75                  80                  85 cag ttg caa cta cct gat aat gaa gta gct caa ata tct gat tac tat        344
Gln Leu Gln Leu Pro Asp Asn Glu Val Ala Gln Ile Ser Asp Tyr Tyr
         90                  95                 100 ccg cgg aat tcg att gat aca aaa gag tat aaa agt acg tta acg tac        392
Pro Arg Asn Ser Ile Asp Thr Lys Glu Tyr Lys Ser Thr Leu Thr Tyr
    105                 110                 115 gga ttc aac ggt aac ctt act ggt gat gat act agt aaa att gga ggc        440
Gly Phe Asn Gly Asn Leu Thr Gly Asp Asp Thr Ser Lys Ile Gly Gly
120                 125                 130
```

-continued ctt att ggg gcc cag gtt tcc cta ggt cat aca ctt aag tat gtt caa 488
Leu Ile Gly Ala Gln Val Ser Leu Gly His Thr Leu Lys Tyr Val Gln
135 140 145 150 cct gat ttc aaa aca att ctc gag agc cca act gat aaa aaa gta ggc 536
Pro Asp Phe Lys Thr Ile Leu Glu Ser Pro Thr Asp Lys Lys Val Gly
155 160 165 tgg aaa gtg ata ttt aac aat atg gtg aat caa aat tgg gga cca tac 584
Trp Lys Val Ile Phe Asn Asn Met Val Asn Gln Asn Trp Gly Pro Tyr
170 175 180 gat cga gat tct tgg aac ccg gta tat ggc aat caa ctt ttc atg aag 632
Asp Arg Asp Ser Trp Asn Pro Val Tyr Gly Asn Gln Leu Phe Met Lys
185 190 195 act aga aat ggt tct atg aaa gca gca gat aac ttc ctt gat cct aac 680
Thr Arg Asn Gly Ser Met Lys Ala Ala Asp Asn Phe Leu Asp Pro Asn
200 205 210 aaa gca agt tcc cta tta tct tca ggg ttt tca cca gac ttc gct aca 728
Lys Ala Ser Ser Leu Leu Ser Ser Gly Phe Ser Pro Asp Phe Ala Thr
215 220 225 230 gtt att act atg gat aga aaa gca tcc aaa caa caa aca aat ata gat 776
Val Ile Thr Met Asp Arg Lys Ala Ser Lys Gln Gln Thr Asn Ile Asp
235 240 245 gta ata tac gaa cga gtt cgt gat gat tac caa ttg cat tgg act tca 824
Val Ile Tyr Glu Arg Val Arg Asp Asp Tyr Gln Leu His Trp Thr Ser
250 255 260 cca aat tgg aaa ggt acc aat act aaa gat aaa tgg aca gat cgt tct 872
Pro Asn Trp Lys Gly Thr Asn Thr Lys Asp Lys Trp Thr Asp Arg Ser
265 270 275 tca gaa aga tat aaa atc gat tgg gaa aaa gaa gaa atg aca aat taa 920
Ser Glu Arg Tyr Lys Ile Asp Trp Glu Lys Glu Glu Met Thr Asn
280 285 290 tgtaanttat ttgtacatgt acaaataaat ataatttata actttagccg aagctggatc 980
cggctgctac naancccnaa ngnagctgan ttgnctgctg ccccccctgac natactagca 1040 naccccttgg gnccctaacg ggtctgnggg gtttttgctg aangngnact tttccgnnan 1100
tcnncccggn ccccccnggt gaaatccnaa nccccnaacn ggngntgnta ncaantttan 1160
tggnncntna ntttnnaaan cnnntaantt ngnaanccccc nttttncnan ggcnaannnn 1220 nanccttta naaaaaancc nnngggggggg tttcnntnnn annnccnttn aangggcccc 1280
cnnggggnaa nnntnggggn 1300

<210> SEQ ID NO 6
<211> LENGTH: 293
<212> TYPE: PRT
<213> ORGANISM: Artificial sequence
<220> FEATURE:
<221> NAME/KEY: misc_feature
<222> LOCATION: (5)..(5)
<223> OTHER INFORMATION: The 'Xaa' at location 5 stands for Leu, or Phe.
<220> FEATURE:
<221> NAME/KEY: misc_feature
<222> LOCATION: (7)..(7)
<223> OTHER INFORMATION: The 'Xaa' at location 7 stands for Tyr, Trp, Cys, Ser, Leu, or Phe.
<220> FEATURE:
<223> OTHER INFORMATION: M113K alpha hemolysin mutant

<400> SEQUENCE: 6

Gln Ile Leu Ile Xaa Thr Xaa Ala Thr Gly Thr Thr Asp Ile Gly Ser
1 5 10 15

Asn Thr Thr Val Lys Thr Gly Asp Leu Val Thr Tyr Asp Lys Glu Asn
20 25 30

Gly Met His Lys Lys Val Phe Tyr Ser Phe Ile Asp Lys Asn His
            35                  40                  45

Asn Lys Lys Leu Leu Val Ile Arg Thr Lys Gly Thr Ile Ala Gly Gln
 50                  55                  60

Tyr Arg Val Tyr Ser Glu Glu Gly Ala Asn Lys Ser Gly Leu Ala Trp
 65                  70                  75                  80

Pro Ser Ala Phe Lys Val Gln Leu Gln Leu Pro Asp Asn Glu Val Ala
                 85                  90                  95

Gln Ile Ser Asp Tyr Tyr Pro Arg Asn Ser Ile Asp Thr Lys Glu Tyr
            100                 105                 110

Lys Ser Thr Leu Thr Tyr Gly Phe Asn Gly Asn Leu Thr Gly Asp Asp
            115                 120                 125

Thr Ser Lys Ile Gly Gly Leu Ile Gly Ala Gln Val Ser Leu Gly His
130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Pro Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

```
<210> SEQ ID NO 7
<211> LENGTH: 1300
<212> TYPE: DNA
<213> ORGANISM: Artificial sequence
<220> FEATURE:
<223> OTHER INFORMATION: M113R alpha hemolysin mutant
<220> FEATURE:
<221> NAME/KEY: CDS
<222> LOCATION: (39)..(920)
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (926)..(926)
<223> OTHER INFORMATION: n is a, c, g, or t
<220> FEATURE:
<221> NAME/KEY: misc_feature
```

```
<222> LOCATION: (991)..(991)
<223> OTHER INFORMATION: n is a, c, g, or t
<220> FEATURE:
<221> NAME/KEY: misc_feature
<222> LOCATION: (994)..(994)
<223> OTHER INFORMATION: n is a, c, g, or t
<220> FEATURE:
<221> NAME/KEY: misc_feature
<222> LOCATION: (998)..(998)
<223> OTHER INFORMATION: n is a, c, g, or t
<220> FEATURE:
<221> NAME/KEY: misc_feature
<222> LOCATION: (1001)..(1001)
<223> OTHER INFORMATION: n is a, c, g, or t
<220> FEATURE:
<221> NAME/KEY: misc_feature
<222> LOCATION: (1003)..(1003)
<223> OTHER INFORMATION: n is a, c, g, or t
<220> FEATURE:
<221> NAME/KEY: misc_feature
<222> LOCATION: (1010)..(1010)
<223> OTHER INFORMATION: n is a, c, g, or t
<220> FEATURE:
<221> NAME/KEY: misc_feature
<222> LOCATION: (1014)..(1014)
<223> OTHER INFORMATION: n is a, c, g, or t
<220> FEATURE:
<221> NAME/KEY: misc_feature
<222> LOCATION: (1031)..(1031)
<223> OTHER INFORMATION: n is a, c, g, or t
<220> FEATURE:
<221> NAME/KEY: misc_feature
<222> LOCATION: (1041)..(1041)
<223> OTHER INFORMATION: n is a, c, g, or t
<220> FEATURE:
<221> NAME/KEY: misc_feature
<222> LOCATION: (1052)..(1052)
<223> OTHER INFORMATION: n is a, c, g, or t
<220> FEATURE:
<221> NAME/KEY: misc_feature
<222> LOCATION: (1067)..(1067)
<223> OTHER INFORMATION: n is a, c, g, or t
<220> FEATURE:
<221> NAME/KEY: misc_feature
<222> LOCATION: (1083)..(1083)
<223> OTHER INFORMATION: n is a, c, g, or t
<220> FEATURE:
<221> NAME/KEY: misc_feature
<222> LOCATION: (1085)..(1085)
<223> OTHER INFORMATION: n is a, c, g, or t
<220> FEATURE:
<221> NAME/KEY: misc_feature
<222> LOCATION: (1087)..(1087)
<223> OTHER INFORMATION: n is a, c, g, or t
<220> FEATURE:
<221> NAME/KEY: misc_feature
<222> LOCATION: (1097)..(1098)
<223> OTHER INFORMATION: n is a, c, g, or t
<220> FEATURE:
<221> NAME/KEY: misc_feature
<222> LOCATION: (1100)..(1100)
<223> OTHER INFORMATION: n is a, c, g, or t
<220> FEATURE:
<221> NAME/KEY: misc_feature
<222> LOCATION: (1103)..(1104)
<223> OTHER INFORMATION: n is a, c, g, or t
<220> FEATURE:
<221> NAME/KEY: misc_feature
<222> LOCATION: (1110)..(1110)
<223> OTHER INFORMATION: n is a, c, g, or t
<220> FEATURE:
<221> NAME/KEY: misc_feature
<222> LOCATION: (1117)..(1117)
<223> OTHER INFORMATION: n is a, c, g, or t
<220> FEATURE:
<221> NAME/KEY: misc_feature
<222> LOCATION: (1128)..(1128)
<223> OTHER INFORMATION: n is a, c, g, or t
<220> FEATURE:
```

```
<221> NAME/KEY: misc_feature
<222> LOCATION: (1131)..(1131)
<223> OTHER INFORMATION: n is a, c, g, or t
<220> FEATURE:
<221> NAME/KEY: misc_feature
<222> LOCATION: (1136)..(1136)
<223> OTHER INFORMATION: n is a, c, g, or t
<220> FEATURE:
<221> NAME/KEY: misc_feature
<222> LOCATION: (1140)..(1140)
<223> OTHER INFORMATION: n is a, c, g, or t
<220> FEATURE:
<221> NAME/KEY: misc_feature
<222> LOCATION: (1143)..(1143)
<223> OTHER INFORMATION: n is a, c, g, or t
<220> FEATURE:
<221> NAME/KEY: misc_feature
<222> LOCATION: (1145)..(1145)
<223> OTHER INFORMATION: n is a, c, g, or t
<220> FEATURE:
<221> NAME/KEY: misc_feature
<222> LOCATION: (1148)..(1148)
<223> OTHER INFORMATION: n is a, c, g, or t
<220> FEATURE:
<221> NAME/KEY: misc_feature
<222> LOCATION: (1151)..(1151)
<223> OTHER INFORMATION: n is a, c, g, or t
<220> FEATURE:
<221> NAME/KEY: misc_feature
<222> LOCATION: (1155)..(1155)
<223> OTHER INFORMATION: n is a, c, g, or t
<220> FEATURE:
<221> NAME/KEY: misc_feature
<222> LOCATION: (1160)..(1160)
<223> OTHER INFORMATION: n is a, c, g, or t
<220> FEATURE:
<221> NAME/KEY: misc_feature
<222> LOCATION: (1164)..(1165)
<223> OTHER INFORMATION: n is a, c, g, or t
<220> FEATURE:
<221> NAME/KEY: misc_feature
<222> LOCATION: (1167)..(1167)
<223> OTHER INFORMATION: n is a, c, g, or t
<220> FEATURE:
<221> NAME/KEY: misc_feature
<222> LOCATION: (1169)..(1169)
<223> OTHER INFORMATION: n is a, c, g, or t
<220> FEATURE:
<221> NAME/KEY: misc_feature
<222> LOCATION: (1171)..(1171)
<223> OTHER INFORMATION: n is a, c, g, or t
<220> FEATURE:
<221> NAME/KEY: misc_feature
<222> LOCATION: (1175)..(1176)
<223> OTHER INFORMATION: n is a, c, g, or t
<220> FEATURE:
<221> NAME/KEY: misc_feature
<222> LOCATION: (1180)..(1180)
<223> OTHER INFORMATION: n is a, c, g, or t
<220> FEATURE:
<221> NAME/KEY: misc_feature
<222> LOCATION: (1182)..(1184)
<223> OTHER INFORMATION: n is a, c, g, or t
<220> FEATURE:
<221> NAME/KEY: misc_feature
<222> LOCATION: (1188)..(1188)
<223> OTHER INFORMATION: n is a, c, g, or t
<220> FEATURE:
<221> NAME/KEY: misc_feature
<222> LOCATION: (1191)..(1191)
<223> OTHER INFORMATION: n is a, c, g, or t
<220> FEATURE:
<221> NAME/KEY: misc_feature
<222> LOCATION: (1193)..(1193)
<223> OTHER INFORMATION: n is a, c, g, or t
<220> FEATURE:
<221> NAME/KEY: misc_feature
<222> LOCATION: (1196)..(1196)
<223> OTHER INFORMATION: n is a, c, g, or t
```

-continued

```
<220> FEATURE:
<221> NAME/KEY: misc_feature
<222> LOCATION: (1201)..(1201)
<223> OTHER INFORMATION: n is a, c, g, or t
<220> FEATURE:
<221> NAME/KEY: misc_feature
<222> LOCATION: (1206)..(1206)
<223> OTHER INFORMATION: n is a, c, g, or t
<220> FEATURE:
<221> NAME/KEY: misc_feature
<222> LOCATION: (1208)..(1208)
<223> OTHER INFORMATION: n is a, c, g, or t
<220> FEATURE:
<221> NAME/KEY: misc_feature
<222> LOCATION: (1210)..(1210)
<223> OTHER INFORMATION: n is a, c, g, or t
<220> FEATURE:
<221> NAME/KEY: misc_feature
<222> LOCATION: (1214)..(1214)
<223> OTHER INFORMATION: n is a, c, g, or t
<220> FEATURE:
<221> NAME/KEY: misc_feature
<222> LOCATION: (1217)..(1221)
<223> OTHER INFORMATION: n is a, c, g, or t
<220> FEATURE:
<221> NAME/KEY: misc_feature
<222> LOCATION: (1223)..(1223)
<223> OTHER INFORMATION: n is a, c, g, or t
<220> FEATURE:
<221> NAME/KEY: misc_feature
<222> LOCATION: (1229)..(1229)
<223> OTHER INFORMATION: n is a, c, g, or t
<220> FEATURE:
<221> NAME/KEY: misc_feature
<222> LOCATION: (1231)..(1231)
<223> OTHER INFORMATION: n is a, c, g, or t
<220> FEATURE:
<221> NAME/KEY: misc_feature
<222> LOCATION: (1238)..(1238)
<223> OTHER INFORMATION: n is a, c, g, or t
<220> FEATURE:
<221> NAME/KEY: misc_feature
<222> LOCATION: (1241)..(1243)
<223> OTHER INFORMATION: n is a, c, g, or t
<220> FEATURE:
<221> NAME/KEY: misc_feature
<222> LOCATION: (1255)..(1256)
<223> OTHER INFORMATION: n is a, c, g, or t
<220> FEATURE:
<221> NAME/KEY: misc_feature
<222> LOCATION: (1258)..(1260)
<223> OTHER INFORMATION: n is a, c, g, or t
<220> FEATURE:
<221> NAME/KEY: misc_feature
<222> LOCATION: (1262)..(1264)
<223> OTHER INFORMATION: n is a, c, g, or t
<220> FEATURE:
<221> NAME/KEY: misc_feature
<222> LOCATION: (1267)..(1267)
<223> OTHER INFORMATION: n is a, c, g, or t
<220> FEATURE:
<221> NAME/KEY: misc_feature
<222> LOCATION: (1270)..(1270)
<223> OTHER INFORMATION: n is a, c, g, or t
<220> FEATURE:
<221> NAME/KEY: misc_feature
<222> LOCATION: (1273)..(1273)
<223> OTHER INFORMATION: n is a, c, g, or t
<220> FEATURE:
<221> NAME/KEY: misc_feature
<222> LOCATION: (1282)..(1283)
<223> OTHER INFORMATION: n is a, c, g, or t
<220> FEATURE:
<221> NAME/KEY: misc_feature
<222> LOCATION: (1288)..(1288)
<223> OTHER INFORMATION: n is a, c, g, or t
<220> FEATURE:
<221> NAME/KEY: misc_feature
<222> LOCATION: (1291)..(1293)
```

<223> OTHER INFORMATION: n is a, c, g, or t
<220> FEATURE:
<221> NAME/KEY: misc_feature
<222> LOCATION: (1295)..(1295)
<223> OTHER INFORMATION: n is a, c, g, or t
<220> FEATURE:
<221> NAME/KEY: misc_feature
<222> LOCATION: (1300)..(1300)
<223> OTHER INFORMATION: n is a, c, g, or t

<400> SEQUENCE: 7

```
gttctgttta actttaagaa gggagatata catatgag cag att ctg ata ttn acn        56
                                         Gln Ile Leu Ile Xaa Thr
                                          1               5 tnn gcg acc ggt act aca gat att gga agc aat act aca gta aaa aca       104
Xaa Ala Thr Gly Thr Thr Asp Ile Gly Ser Asn Thr Thr Val Lys Thr
         10                  15                  20 ggt gat tta gtc act tat gat aaa gaa aat ggc atg cac aaa aaa gta       152
Gly Asp Leu Val Thr Tyr Asp Lys Glu Asn Gly Met His Lys Lys Val
     25                  30                  35 ttt tat agt ttt atc gat gat aaa aat cac aat aaa aaa ctg cta gtt       200
Phe Tyr Ser Phe Ile Asp Asp Lys Asn His Asn Lys Lys Leu Leu Val
 40                  45                  50 att aga aca aaa ggt acc att gct ggt caa tat aga gtt tat agc gaa       248
Ile Arg Thr Lys Gly Thr Ile Ala Gly Gln Tyr Arg Val Tyr Ser Glu
 55                  60                  65                  70 gaa ggt gct aac aaa agt ggt tta gcc tgg cct tca gcc ttt aag gta       296
Glu Gly Ala Asn Lys Ser Gly Leu Ala Trp Pro Ser Ala Phe Lys Val
             75                  80                  85 cag ttg caa cta cct gat aat gaa gta gct caa ata tct gat tac tat       344
Gln Leu Gln Leu Pro Asp Asn Glu Val Ala Gln Ile Ser Asp Tyr Tyr
         90                  95                 100 ccg cgg aat tcg att gat aca aaa gag tat aga agt acg tta acg tac       392
Pro Arg Asn Ser Ile Asp Thr Lys Glu Tyr Arg Ser Thr Leu Thr Tyr
     105                 110                 115 gga ttc aac ggt aac ctt act ggt gat gat act agt aaa att gga ggc       440
Gly Phe Asn Gly Asn Leu Thr Gly Asp Asp Thr Ser Lys Ile Gly Gly
 120                 125                 130 ctt att ggg gcc cag gtt tcc cta ggt cat aca ctt aag tat gtt caa       488
Leu Ile Gly Ala Gln Val Ser Leu Gly His Thr Leu Lys Tyr Val Gln
135                 140                 145                 150 cct gat ttc aaa aca att ctc gag agc cca act gat aaa aaa gta ggc       536
Pro Asp Phe Lys Thr Ile Leu Glu Ser Pro Thr Asp Lys Lys Val Gly
             155                 160                 165 tgg aaa gtg ata ttt aac aat atg gtg aat caa aat tgg gga cca tac       584
Trp Lys Val Ile Phe Asn Asn Met Val Asn Gln Asn Trp Gly Pro Tyr
         170                 175                 180 gat cga gat tct tgg aac ccg gta tat ggc aat caa ctt ttc atg aag       632
Asp Arg Asp Ser Trp Asn Pro Val Tyr Gly Asn Gln Leu Phe Met Lys
     185                 190                 195 act aga aat ggt tct atg aaa gca gca gat aac ttc ctt gat cct aac       680
Thr Arg Asn Gly Ser Met Lys Ala Ala Asp Asn Phe Leu Asp Pro Asn
 200                 205                 210 aaa gca agt tcc cta tta tct tca ggg ttt tca cca gac ttc gct aca       728
Lys Ala Ser Ser Leu Leu Ser Ser Gly Phe Ser Pro Asp Phe Ala Thr
215                 220                 225                 230 gtt att act atg gat aga aaa gca tcc aaa caa caa aca aat ata gat       776
Val Ile Thr Met Asp Arg Lys Ala Ser Lys Gln Gln Thr Asn Ile Asp
             235                 240                 245 gta ata tac gaa cga gtt cgt gat gat tac caa ttg cat tgg act tca       824
Val Ile Tyr Glu Arg Val Arg Asp Asp Tyr Gln Leu His Trp Thr Ser
         250                 255                 260
```

```
cca aat tgg aaa ggt acc aat act aaa gat aaa tgg aca gat cgt tct      872
Pro Asn Trp Lys Gly Thr Asn Thr Lys Asp Lys Trp Thr Asp Arg Ser
        265                 270                 275 tca gaa aga tat aaa atc gat tgg gaa aaa gaa gaa atg aca aat taa      920
Ser Glu Arg Tyr Lys Ile Asp Trp Glu Lys Glu Glu Met Thr Asn
    280                 285                 290 tgtaanttat ttgtacatgt acaaataaat ataatttata actttagccg aagctggatc    980
cggctgctac naanccnaa ngnagctgan ttgnctgctg cccccctgac natactagca    1040
naccccttgg gnccctaacg ggtctgnggg gttttttgctg aangngnact tttccgnnan    1100
tcnncccggn ccccccnggt gaaatccnaa ncccnaacn ggngntgnta ncaantttan     1160
tggnncntna ntttnnaaan cnnntaantt ngnaancccc nttttncnan ggcnaannnn    1220 nanccttna naaaaaance nnnggggggg tttcnntnnn annnccnttn aanggggccc     1280 cnngggnaa nnntnggggn                                                 1300

<210> SEQ ID NO 8
<211> LENGTH: 293
<212> TYPE: PRT
<213> ORGANISM: Artificial sequence
<220> FEATURE:
<221> NAME/KEY: misc_feature
<222> LOCATION: (5)..(5)
<223> OTHER INFORMATION: The 'Xaa' at location 5 stands for Leu, or Phe.
<220> FEATURE:
<221> NAME/KEY: misc_feature
<222> LOCATION: (7)..(7)
<223> OTHER INFORMATION: The 'Xaa' at location 7 stands for Tyr, Trp,
      Cys, Ser, Leu, or Phe.
<220> FEATURE:
<223> OTHER INFORMATION: M113R alpha hemolysin mutant

<400> SEQUENCE: 8

```
                195                 200                 205
Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Pro Asn Trp Lys Gly Thr Asn Thr Lys Asp
            260                 265                 270

Lys Trp Thr Asp Arg Ser Ser Glu Arg Tyr Lys Ile Asp Trp Glu Lys
                275                 280                 285

Glu Glu Met Thr Asn
        290

<210> SEQ ID NO 9
<211> LENGTH: 228
<212> TYPE: PRT
<213> ORGANISM: Artificial sequence
<220> FEATURE:
<223> OTHER INFORMATION: Lambda exonuclease

<400> SEQUENCE: 9

Ser His Met Thr Pro Asp Ile Ile Leu Gln Arg Thr Gly Ile Asp Val
1               5                   10                  15

Arg Ala Val Glu Gln Gly Asp Asp Ala Trp His Lys Leu Arg Leu Gly
                20                  25                  30

Val Ile Thr Ala Ser Glu Val His Asn Val Ile Ala Lys Pro Arg Ser
            35                  40                  45

Gly Lys Lys Trp Pro Asp Met Lys Met Ser Tyr Phe His Thr Leu Leu
    50                  55                  60

Ala Glu Val Cys Thr Gly Val Ala Pro Glu Val Asn Ala Lys Ala Leu
65                  70                  75                  80

Ala Trp Gly Lys Gln Tyr Glu Asn Asp Ala Arg Thr Leu Phe Glu Phe
                85                  90                  95

Thr Ser Gly Val Asn Val Thr Glu Ser Pro Ile Ile Tyr Arg Asp Glu
            100                 105                 110

Ser Met Arg Thr Ala Cys Ser Pro Asp Gly Leu Cys Ser Asp Gly Asn
        115                 120                 125

Gly Leu Glu Leu Lys Cys Pro Phe Thr Ser Arg Asp Phe Met Lys Phe
    130                 135                 140

Arg Leu Gly Gly Phe Glu Ala Ile Lys Ser Ala Tyr Met Ala Gln Val
145                 150                 155                 160

Gln Tyr Ser Met Trp Val Thr Arg Lys Asn Ala Trp Tyr Phe Ala Asn
                165                 170                 175

Tyr Asp Pro Arg Met Lys Arg Glu Gly Leu His Tyr Val Val Ile Glu
            180                 185                 190

Arg Asp Glu Lys Tyr Met Ala Ser Phe Asp Glu Ile Val Pro Glu Phe
        195                 200                 205

Ile Glu Lys Met Asp Glu Ala Leu Ala Glu Ile Gly Phe Val Phe Gly
    210                 215                 220

Glu Gln Trp Arg
225
```